US006648306B2

(12) United States Patent
Rock

(10) Patent No.: US 6,648,306 B2
(45) Date of Patent: Nov. 18, 2003

(54) FLUID PROCESSING SYSTEM AND METHOD

(75) Inventor: Kelly P. Rock, Orlando, FL (US)

(73) Assignee: LyteSyde, LLC, San Clemente, CA (US)

(*) Notice: Subject to any disclaimer, the term of this patent is extended or adjusted under 35 U.S.C. 154(b) by 0 days.

(21) Appl. No.: 10/078,731

(22) Filed: Feb. 18, 2002

(65) Prior Publication Data

US 2002/0089072 A1 Jul. 11, 2002

Related U.S. Application Data

(60) Continuation of application No. 09/532,171, filed on Mar. 20, 2000, now Pat. No. 6,347,789, which is a division of application No. 09/040,666, filed on Mar. 18, 1998, now Pat. No. 6,113,078.

(51) Int. Cl.[7] .............................. B01F 3/04; F02M 29/06
(52) U.S. Cl. ............... 261/79.1; 261/79.2; 261/DIG. 55
(58) Field of Search ............................ 261/79.1, 79.2, 261/78.1, 78.2, 62, 65, DIG. 55

(56) References Cited

U.S. PATENT DOCUMENTS

| 634,242 A | 10/1899 | Lambert | 261/79.1 X |
|---|---|---|---|
| 751,292 A | 2/1904 | Johanson | 261/79.1 X |
| 860,259 A | 7/1907 | Smith | 261/79.1 X |
| 1,163,437 A | * 12/1915 | Morison | 261/79.2 X |
| 1,233,557 A | 7/1917 | Curtis | 261/79.1 X |
| 1,309,719 A | 7/1919 | Curtis | 261/79.1 X |
| 1,313,521 A | 8/1919 | Connor | 261/79.1 X |
| 1,451,063 A | * 4/1923 | Anthony | 261/79.2 X |
| 1,471,220 A | * 10/1923 | Tangye | 261/79.1 |
| 1,626,085 A | 4/1927 | Henriot | 261/79.1 X |
| 2,071,717 A | 2/1937 | Winkle | 261/79.1 X |
| 2,599,422 A | 6/1952 | Yettaw | 299/140 |
| 3,286,997 A | 11/1966 | Ledbetter | 261/79.1 X |
| 3,336,017 A | 8/1967 | Kopa | 261/79.1 X |
| 3,395,899 A | * 8/1968 | Kopa | 261/79.1 X |
| 3,414,242 A | 12/1968 | Bouteleux | 261/79.1 X |

(List continued on next page.)

FOREIGN PATENT DOCUMENTS

| DE | 1108666 | 6/1961 | 261/79.2 |
|---|---|---|---|
| DE | 35 11 094 A1 | 10/1986 | |
| DE | G94 02 811.7 | 7/1994 | |
| DE | 44 27 466 A1 | 2/1996 | |
| FR | 746984 | 6/1933 | 261/79.1 |
| FR | 1156341 | 5/1958 | 261/79.2 |
| GB | 2 296 037 A | 6/1996 | |
| SU | 1357032 | 12/1987 | 261/79.2 |
| WO | WO 85/03741 | 8/1985 | |

Primary Examiner—Richard L. Chiesa
(74) Attorney, Agent, or Firm—Holland & Hart

(57) ABSTRACT

This disclosure relates to a centrifugal vortex system for preparing a liquid, such as fuel and includes a chamber housing defining a vortex chamber. An array of tangential apertures are formed in the chamber housing to permit fluid to be turbulently introduced into the vortex chamber to create a vortical flow of fluid through the vortex chamber. In one embodiment, a plurality of vortex chambers are arranged in series to allow the fluid to pass through several vortex chambers. In other embodiments, the chamber housing may be stepped, textured, or both to increase the turbulence of the flow through the chamber. In yet another embodiment, a pressure differential supply jacket is provided to normalize the amount of flow through the tangential apertures according to the location of the apertures. A centrifuge chamber is also disclosed which has a plurality of output conduits on a bottom surface and a tapered extension member downwardly extending from a top surface to enhance the centrifugal flow of the fluid. Additionally, a bypass conduit is provided to selectively permit the flow to bypass one or more chambers.

7 Claims, 22 Drawing Sheets

U.S. PATENT DOCUMENTS

| | | | |
|---|---|---|---|
| 3,651,619 A | 3/1972 | Miura | 261/79.2 X |
| 3,667,221 A | 6/1972 | Taylor | 261/79.1 X |
| 3,778,038 A | 12/1973 | Eversole | 261/79.1 X |
| 3,866,585 A | 2/1975 | Kopa | 123/127 |
| 3,944,634 A | 3/1976 | Gerlach | 261/79.1 X |
| 4,087,862 A | 5/1978 | Tsien | 366/184 |
| 4,159,881 A | 7/1979 | Gogneau | 366/337 |
| 4,215,535 A | 8/1980 | Lewis | 261/79.1 X |
| 4,217,313 A | 8/1980 | Dmitrievsky et al. | 261/79.1 X |
| 4,464,314 A | 8/1984 | Surovikin et al. | 261/79.2 |
| 4,515,734 A | 5/1985 | Rock et al. | 261/DIG. 21 |
| 4,568,500 A | 2/1986 | Rock et al. | 261/DIG. 19 |
| 4,726,686 A | 2/1988 | Wolf et al. | 210/512.1 X |
| 4,943,704 A | 7/1990 | Rabenau et al. | 261/79.2 X |
| 5,071,068 A | 12/1991 | Suniewski | 239/8 |
| 5,169,302 A | 12/1992 | Keller | 431/350 |
| 5,340,306 A | 8/1994 | Keller et al. | 431/354 |
| 5,472,645 A | 12/1995 | Rock et al. | 261/79.1 |
| 5,512,216 A | 4/1996 | Rock et al. | 261/79.1 |
| 5,672,187 A | 9/1997 | Rock et al. | 261/79.1 X |
| 6,113,078 A | 9/2000 | Rock | 261/79.1 X |
| 6,244,573 B1 | 6/2001 | Rock | 261/79.1 X |

* cited by examiner

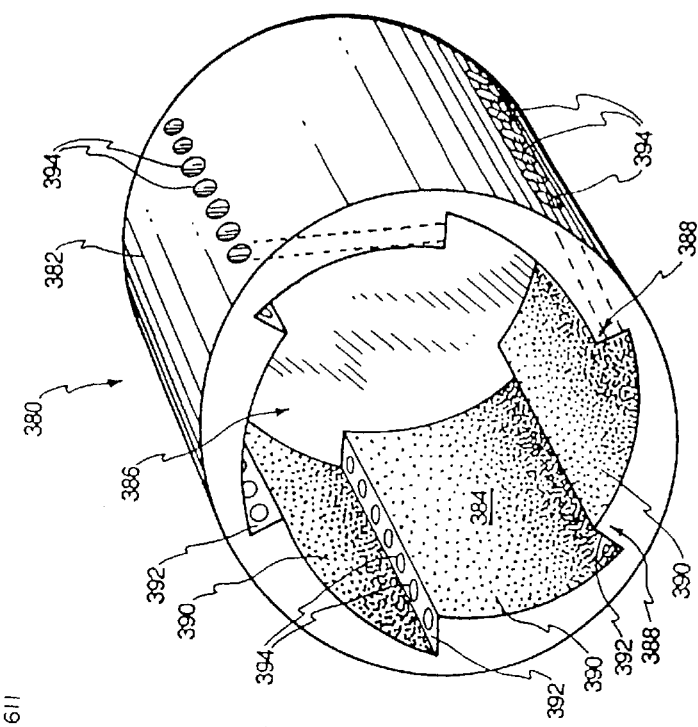
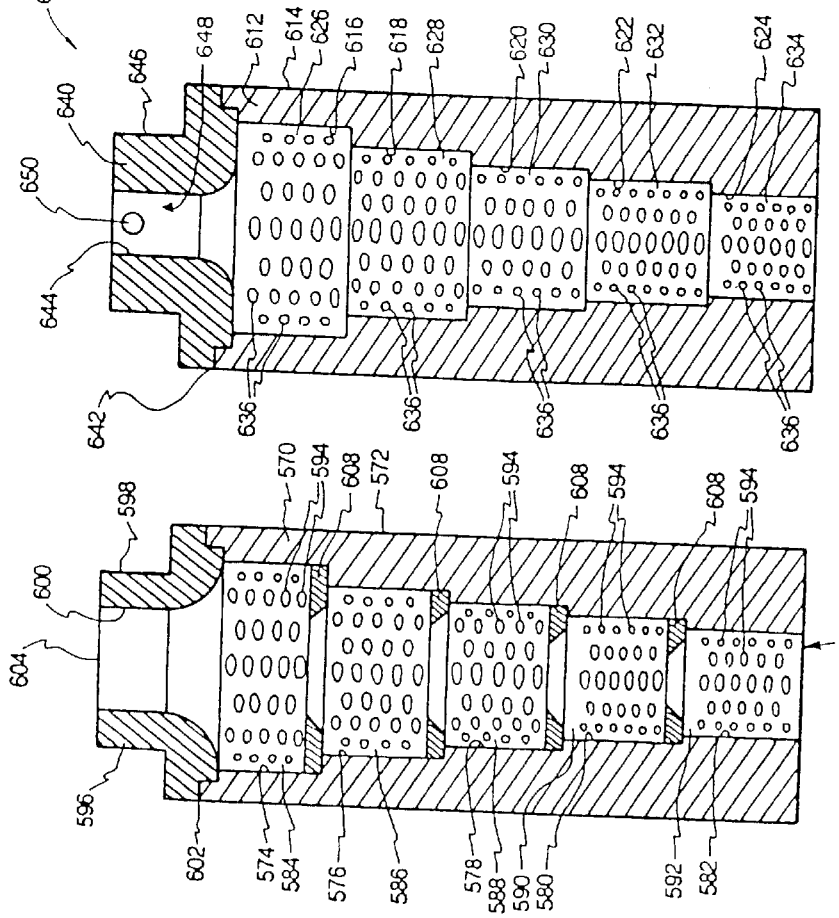

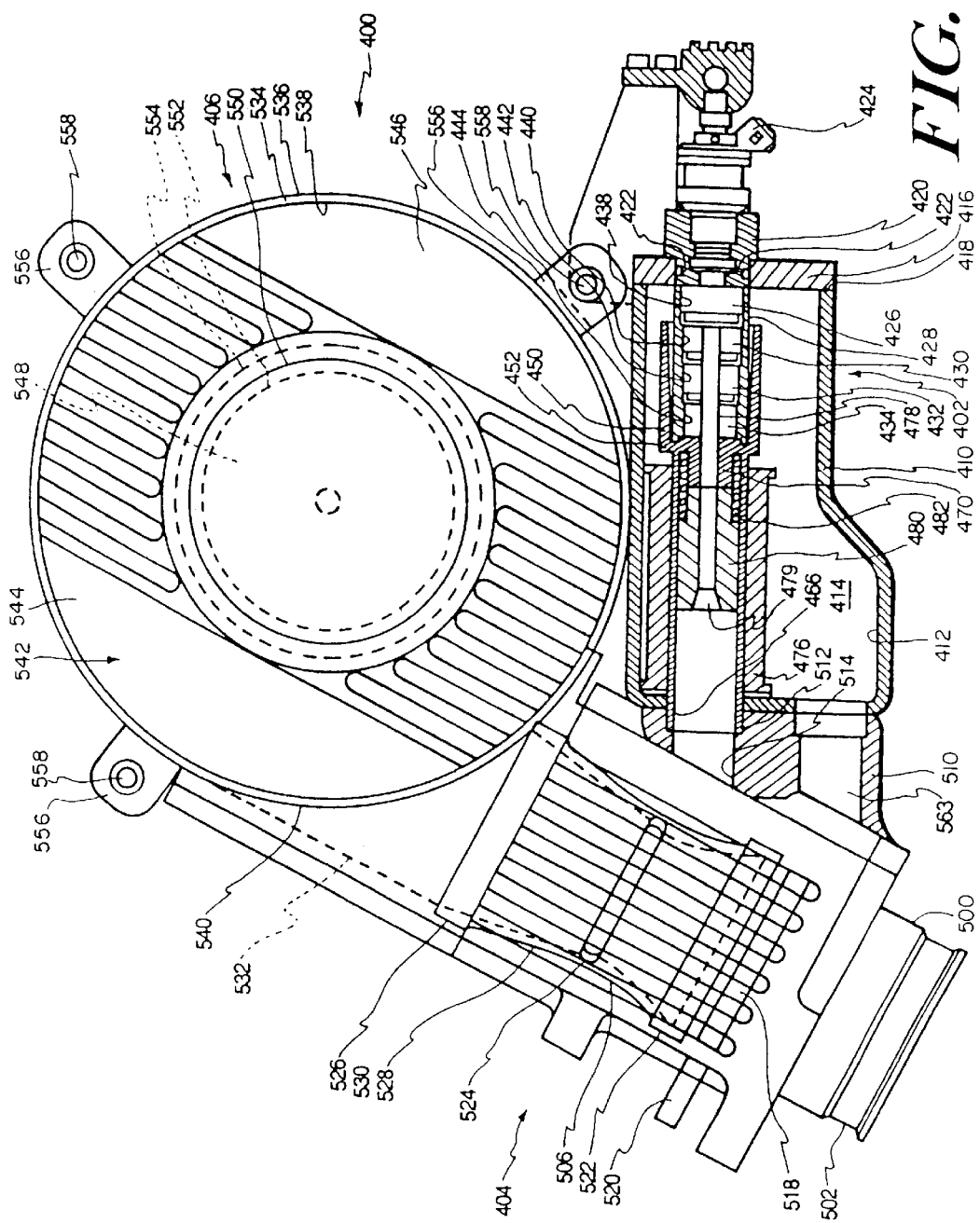

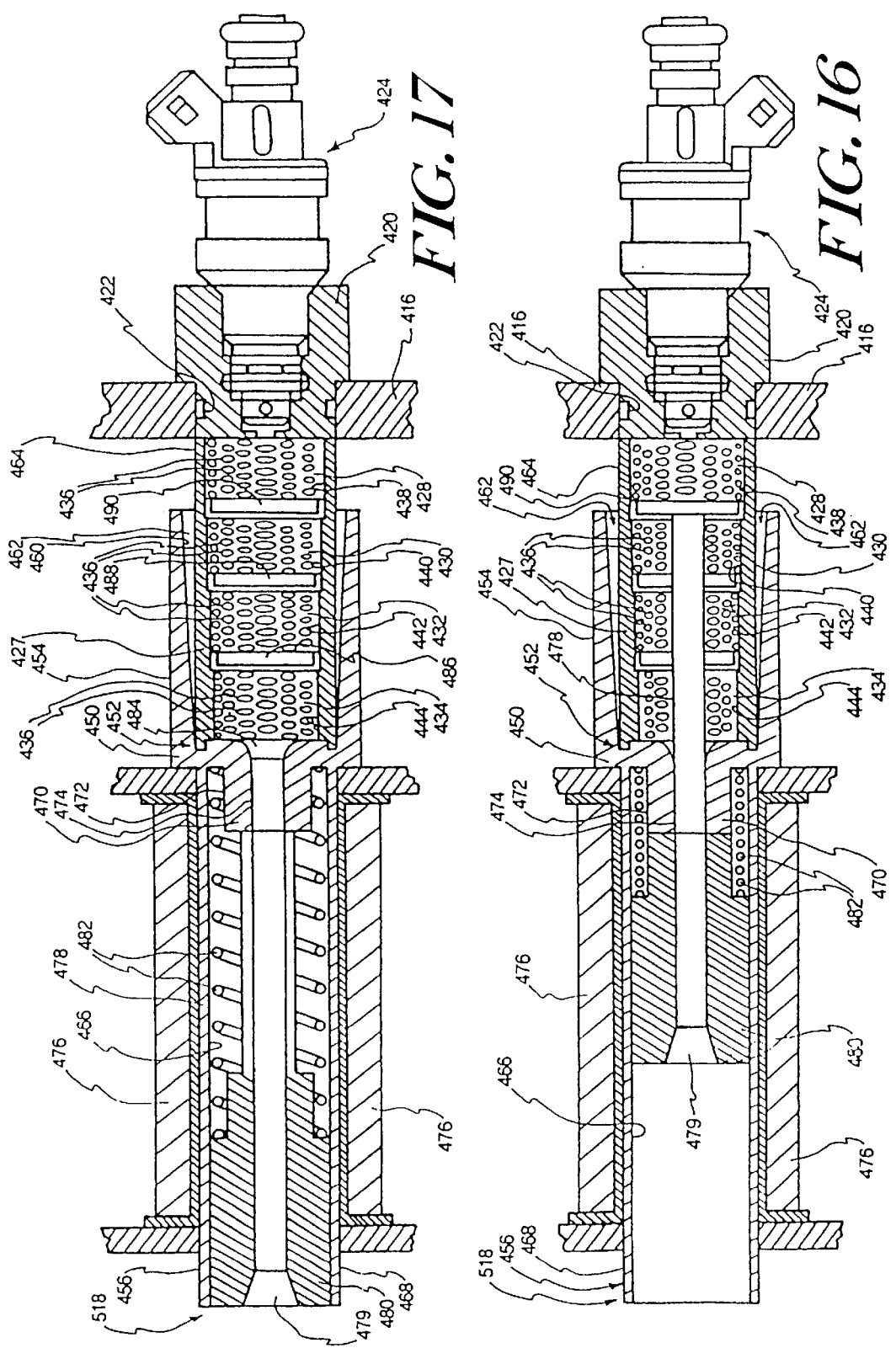

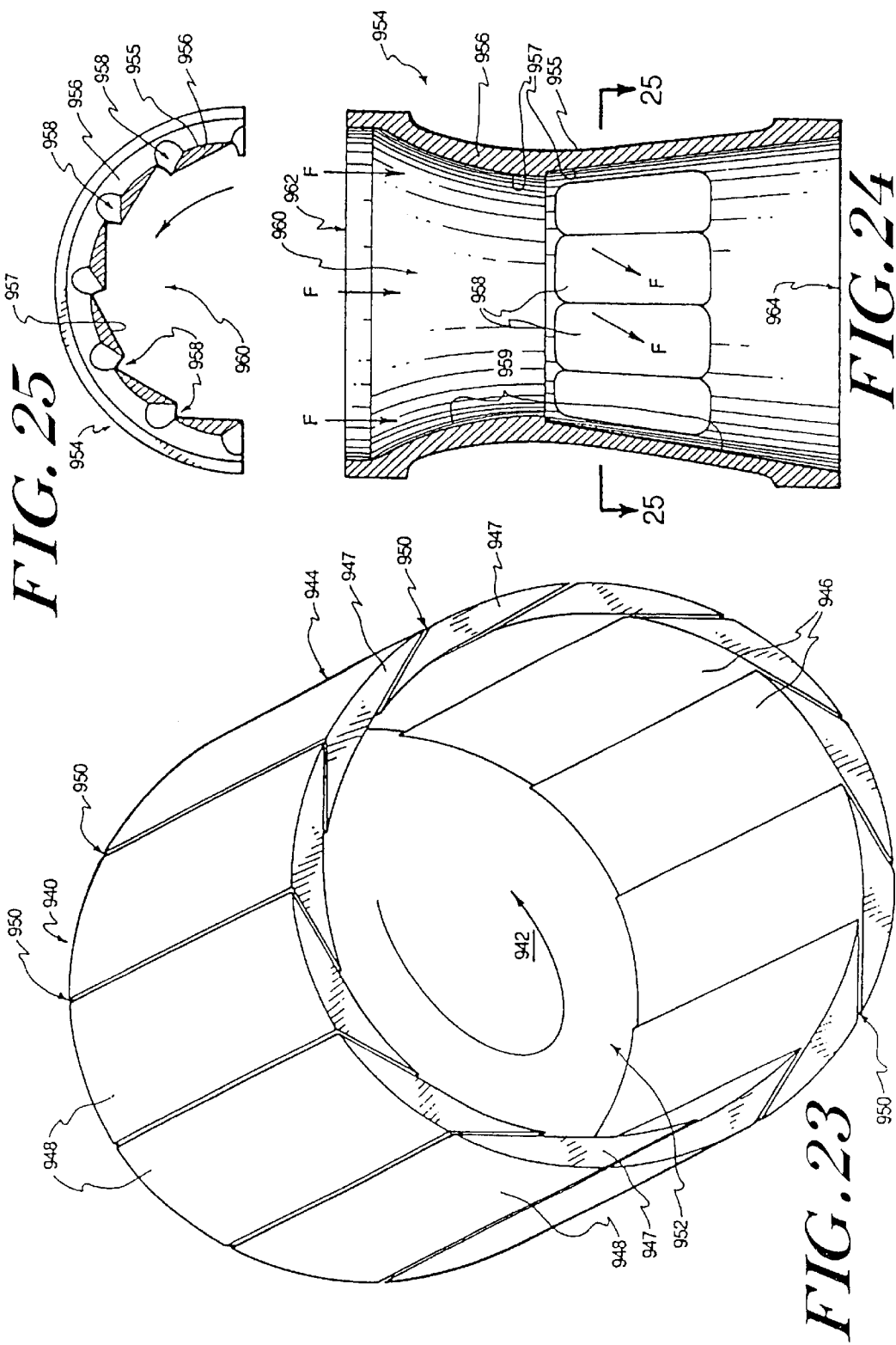

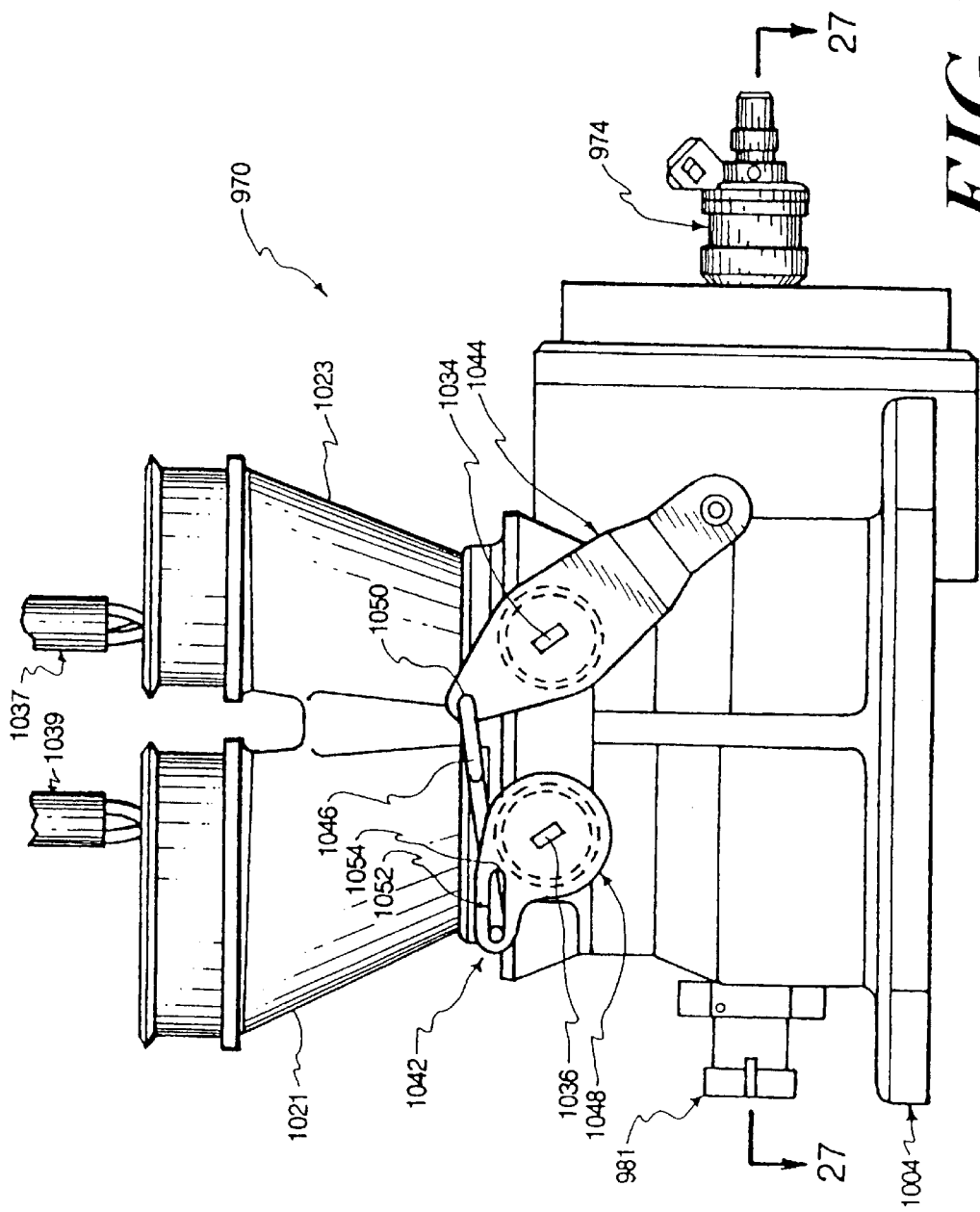

FLUID PROCESSING SYSTEM AND METHOD

CONTINUITY

This is a continuation of U.S. patent application Ser. No. 09/532,171, filed Mar. 20, 2000, now U.S. Pat. No. 6,347,789 which is a divisional of U.S. patent application Ser. No. 09/040,666, filed Mar. 18, 1998, now U.S. Pat. No. 6,113,078.

TECHNICAL FIELD

This invention relates to fluid vaporizing and homogenizing devices, to systems for vaporizing and homogenizing fluids, and more particularly to devices and systems for producing finely homogenized or vaporized gas-phase fluid mixtures.

BACKGROUND OF THE INVENTION

Many types of devices have been developed over the years for the purpose of converting liquids or aerosols into gas-phase fluids. Many such devices have been developed to prepare fuel for use in internal combustion engines. To optimize fuel oxidation within an engine's combustion chamber, the fuel/air mixture commonly must be further vaporized or homogenized to achieve a chemically-stoichiometric gas-phase mixture. Ideal fuel oxidation results in more complete combustion and lower pollution.

More specifically, relative to internal combustion engines, stoichiometricity is a condition where the amount of oxygen required to completely burn a given amount of fuel is supplied in a homogeneous mixture resulting in optimally correct combustion with no residues remaining from incomplete or inefficient oxidation. Ideally, the fuel should be completely vaporized, intermixed with air, and homogenized prior to entering the combustion chamber for proper oxidation. Non-vaporized fuel droplets generally do not ignite and combust completely in conventional internal and external combustion engines, which presents problems relating to fuel efficiency and pollution.

Incomplete or inefficient oxidation of fuel causes exhaustion of residues from the internal or external combustion engine as pollutants, such as unburned hydrocarbons, carbon monoxide, and aldehydes, with accompanying production of oxides of nitrogen. To meet emission standards, these residues must be dealt with, typically requiring further treatment in a catalytic converter or a scrubber. Such treatment of these residues results in additional fuel costs to operate the catalytic converter or scrubber. Accordingly, any reduction in residues resulting from incomplete combustion would be economically and environmentally beneficial.

Aside from the problems discussed above, a fuel-air mixture that is not completely vaporized and chemically stoichiometric causes the combustion engine to perform inefficiently. Since a smaller portion of the fuel's chemical energy is converted to mechanical energy, fuel energy is wasted thereby generating unnecessary heat and pollution. Thus, by further breaking down and more completely vaporizing the fuel-air mixture, higher engine efficiency may be obtained.

Attempts have been made to alleviate the above-described problems with respect to fuel vaporizaton and incomplete fuel combustion. For example, U.S. Pat. No. 4,515,734, U.S. Pat. No. 4,568,500, U.S. Pat. No. 5,512,216, U.S. Pat. No. 5,472,645, and U.S. Pat. No. 5,672,187 disclose various devices which vaporize fuel as it is being provided to the intake manifold of an engine. These prior devices generally involve a series of mixing sites and a venturi for vaporizing fuel and air.

It should be noted that the above-mentioned prior devices provide certain advantages in the operation of a combustion engine by allowing a relatively high degree of hydrocarbon burning in an associated engine. Nevertheless, there are certain problems with these prior devices.

First, the apertures for inputting air into the vortex chambers are arranged in a single column of three apertures. This manner of introducing air into the vortex chambers may cause the fluid within the vortex chamber to separate into discrete rings of fluid along the inner wall of the vortex chamber. Typically, one such ring will be associated with one of the apertures. The tendency for fluids to collect in rings along the vortex chamber walls necessarily limits the degree of turbulence (and thus the efficiency of vaporization) within a given vortex chamber.

Additionally, prior devices have employed vortex chambers that have smooth, cylindrical inner walls. A smooth vortex chamber inner wall construction may limit the degree of turbulence within a given chamber and the effective rate of vaporization within the vortex chambers.

Another perceived shortcoming of prior devices is their inability to compensate for differential pressures at the various inlets leading to the vortex chamber. As the air/fuel mixture passes through the various vortex chambers, additional air is tangentially added in each chamber which causes a pressure differential at the various inlets. By supplying ambient air at all of these inlets to the vortex chamber, it has been difficult to maintain an optimal air-to-fuel ratio of the air/fuel mixture as the mixture passes through the vortex chambers.

Yet another aspect of the pressure differential problem associated with prior known devices is that there is a tendency for the vortex chambers positioned closer to the low pressure end of the flow path (closer to the engine manifold) to dominate the other vortex chambers by receiving substantially more flow. This tendency is particularly noticeable and problematic during periods of engine acceleration. As the vortex chambers closer to low pressure end of the flow path dominate the other vortex chambers, the effectiveness of the other vortex chambers is significantly reduced.

The prior centrifuge vaporization devices also have certain limitations, such as being too voluminous, failing to effectively introduce fluid into the centrifuge chamber tangentially, unnecessarily inhibiting the drawing power of the engine manifold vacuum, and unevenly discharging the centrifuge contents into the engine manifold.

An additional limitation of prior centrifuge vaporization devices has been their failure to adequately mix ambient air with fuel prior to adding the air and fuel into the vortex chamber. Absent adequate air/fuel premixing, excessive hydrocarbons are produced. Prior attempts to solve this problem have proven ineffective in that, even if fuel in a gaseous or aerosol state is sprayed into an air flow stream, the fuel subsequently liquefies prior to entering into the vortex chamber, thus nullifying any advantage obtained by spraying a gaseous or aerosol fuel into an air stream.

A further problem of prior centrifuge vaporization devices has been their failure to provide a venturi configuration which is large enough to attain volumetric efficiencies at high RPM's, yet small enough to get high resolution responses at lower RPM's. Indeed, the prior devices have generally had to choose between volumetric efficiency at high RPM's and high resolution response at lower RPM's. A need exists, therefore, for a centrifuge vaporization device which can attain volumetric efficiency at high RPM's and high resolution response at lower RPM's.

Yet another problem concerning prior cyclone vaporization devices is that they have failed to appreciate or utilize the advantages associated with adjustable vortex chamber output ports and adjacent chambers of different diameters.

Another problem, different from applications of vortex technology to internal combustion engines, relates to the extreme vaporization needed for various medications administered via inhalers. An inhaler typically produces a liquid/gas mixture of the medication for inhaling directly into the lungs. Problems have arisen, however, in that the high degree of vaporization required for directly passing the medication through the lungs into the bloodstream has been difficult to achieve. That is, excess amounts of the medication remain liquefied, rather than being further broken down into smaller molecular size particles, for passing immediately through the lungs into the bloodstream. A need exists, therefore, to develop certain vaporization devices that will further vaporize and homogenize liquid/gas mixtures into a vapor of sufficiently small vapor particles for administering medication directly into the bloodstream via the lungs.

Still another need exists with respect to utilization of a breakdown process for incineration and waste management. To the extent waste fluid particles can be broken down into extremely small particle sizes, a mixture being introduced into a waste disposal or waste treatment device will create a more efficient burn, thereby minimizing pollution and increasing the efficiency by which waste fluids are incinerated.

In view of the foregoing, there is a need to develop a centrifugal vortex system that solves or substantially alleviates the above-discussed limitations associated with known prior devices. There is a need to develop a centrifugal vortex system with a vortex chamber that enables a more optimal turbulent flow, that more completely breaks down liquid into smaller sized particles of vapor fluid, and that normalizes the flow through the various apertures formed in the vortex chamber housing. There is a further need to provide a centrifugal vortex system that more optimally premixes air and fuel prior to introducing the air/fuel mixture into the vortex chamber. Another need exists to provide a low-volume centrifuge apparatus that more optimally mixes, vaporizes, homogenizes, and discharges more minutely sized molecular vapor particles into an engine manifold, from an inhaler-type medicinal administration device, and to/from other desired applications.

SUMMARY AND OBJECTS OF THE INVENTION

It is an object of the invention to provide a vortex chamber that enables a more optimal turbulent flow and which substantially eliminates the formation of liquid orbital rings on the inner walls within the vortex chamber.

Another object of the invention is to provide a plurality of vortex chambers with air being introduced only in the first chamber to maintain a constant air/fuel ratio of the air/fuel mixture as the mixture advances through subsequent chambers.

Another object of the invention is to provide a vortex chamber housing with a stepped inner wall surface for increasing the turbulence of fluid flowing through the vortex chamber.

Another object of the invention is to provide a vortex chamber housing with an irregular or textured inner wall surface for increasing the turbulence of fluid flowing through the vortex chamber.

Another object of the invention is to provide a pressure differential supply, such as a tapered air-feed channel formed perhaps by a jacket, to equalize the amount of flow entering several input apertures formed in a vortex chamber.

Another object of the invention is to provide a series of tangentially oriented baffles associated with a centrifuge chamber to form a series of tangential passageways into the centrifuge chamber to enhance the centrifugal flow of fluid in the centrifuge chamber.

Another object of the invention is to provide a movable conduit which is capable of being inserted through a series of vortex chambers to selectively isolate and bypass one or more of the other chambers.

Another object of the invention is to provide a vortex chamber with an adjustable output port to assist in regulating the flow of fluid through the output port.

Another object of the invention is to provide a centrifuge chamber with a plurality of output ports to homogenize and further vaporize the fluid output flow to the engine.

Another object of the invention is to provide a tapered extension on a top surface of the centrifuge chamber to reduce the chamber volume and to enhance the centrifugal or vortical flow of fluid within the chamber.

Another object of the invention is to increase turbulence within the vortex chamber by reducing the chamber volume and by employing a centrifuge vertical wall with a height less than the maximum inside diameter of an associated venturi.

Another object of the invention is to provide a series of increasing diameter vortex chambers to normalize or equalize the fluid flow in the respective vortex chambers.

Another object of the invention is to provide a venturi and an associated centrifuge chamber where the ratio of the venturi throat diameter to the diameter of the centrifuge output port is approximately 1:1.66.

Another object of the invention is to provide a preliminary mixing chamber to premix the air and the fuel prior to introducing the air/fuel mixture into a vortex chamber for homogenization and vaporization.

Another object of the invention is to provide a more optimal turbulence within a vortex chamber and to achieve improved vaporization by causing a vortical flow to spin in alternative, opposite spin directions as the vortical flow passes from one vortex chamber to an adjacent vortex chamber.

Another object of the present invention is to provide a centrifuge vaporization device which can attain a high volumetric efficiency at high RPM's and high resolution response at lower RPM's.

Still another object of the present invention is to provide a device for breaking down a vapor/gaseous mixture into more minute sized particles on a molecular scale for medical applications.

Still another object of the present invention is to produce a device that allows a vapor/liquid mixture to be broken down into extremely small sized particles such that the particles pass immediately and directly through the lungs into a person's bloodstream.

Yet another object of the present invention is to provide a device that breaks down a flow of fluid comprising liquid and vapor particles such that the fluid flow will burn more optimally in an incinerator.

Still another object of the invention is to provide a device that allows fuel to be homogenized to a degree where a more optimal combustion is achieved thereby reducing pollutants created from the combustion process.

Another object of the invention is to provide a device with an extension arm within a centrifuge housing to prevent a blackflow of fluid out of the centrifuge housing and to enhance the centrifugal flow of fluid in the centrifuge housing.

The foregoing objects are achieved by a centrifugal vortex system that enhances the turbulent flow and the vaporization of a fluid in a vortex chamber by a particular premixing process that combines air and fuel prior to introducing the air/fuel mixture into an array of apertures formed in a vortex chamber housing. The apertures are formed in the vortex chamber housing to cause the air/fuel mixture to be introduced tangentially into the vortex chamber. The flow into the various apertures is equalized by a differential supply configuration that enables effective use of all apertures.

In one embodiment, the inner wall of the vortex chamber housing is stepped or textured, or both, to enhance the turbulence of a flow through the vortex chamber. In another embodiment, the centrifuge chamber has a series of baffles and a tapered extension to enhance the centrifugal flow of fluid in the vortex chamber. In yet another embodiment, an elongated conduit is insertable through a series of vortex chambers to selectively isolate and/or bypass one or more of the chambers. In still another embodiment, the vortex chamber output has an adjustable diameter for regulating the flow through the vortex chamber.

Other objects, features, and advantages of the invention will become apparent from the following detailed description of the invention with reference to the accompanying drawings.

BRIEF DESCRIPTION OF THE DRAWINGS

Preferred embodiments of the invention are described below with reference to the accompanying drawings:

FIG. 14 is a perspective view of an alternative embodiment of a vortex chamber housing according to the present invention;

FIG. 15 is a top partial sectional view of another alternative embodiment of a centrifugal vortex system according to the present invention;

FIG. 16 is an enlarged sectional view of the elongated conduit assembly shown in FIG. 15;

FIG. 17 is an enlarged view of the elongated conduit assembly shown in FIG. 15 with the elongated conduit retracted from the vortex chambers;

FIG. 18 is a sectional view of yet another alternative embodiment of a vortex housing according to the present invention;

FIG. 19 is a sectional view of still another alternative embodiment of a vortex chamber housing according to the present invention;

FIG. 23 is a perspective view of yet another alternative embodiment of a vortex chamber housing according to the present invention;

FIG. 24 is a sectional side elevation view of an alternative embodiment of a venturi according to the present invention;

FIG. 25 is a partial cross-sectional view, taken along the line 25—25 of FIG. 24, of an alternate embodiment of a venturi according to the present invention;

FIG. 26 is a plan view of still another alternate embodiment of a centrifugal vortex system according to the present invention.

DETAILED DESCRIPTION OF THE INVENTION

In the context of this document, the terms "homogenize" or "vaporize" or any derivative of these terms means to convert a liquid from an aerosol or vapor-phase to a gas-phase by vorticular turbulence where high velocity, low pressure, and high vacuum conditions exist, i.e., where differential pressures exist.

Figure 1:
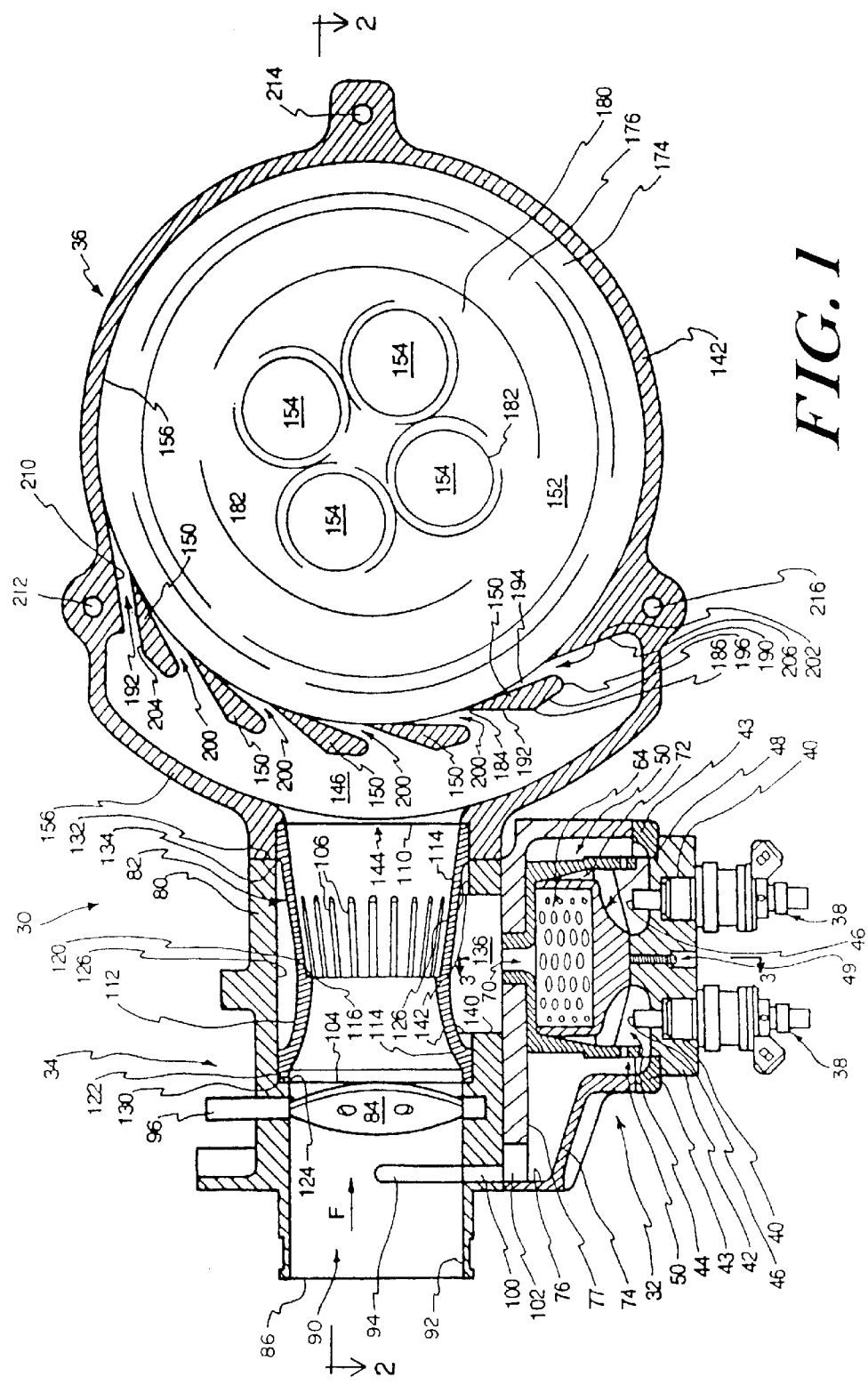
FIG. 1 is a top sectional view of a centrifugal vortex system according to the present invention.

FIGS. 1–6 show a first embodiment of a centrifugal vortex system 30 according to the present invention. As shown in FIG. 1, the centrifugal vortex system 30 has three sections: a fuel vaporizing section 32, a main air section 34, and a centrifuge section 36. The fuel vaporizing section 32 is illustrated as having two fuel injectors 38 mounted in bores 40 formed in an injector plate 42. The fuel injectors 38 may comprise conventional electronic fuel injectors and preferably have a spray angle of about 30°.

A preliminary mixing chamber 44 is formed in the fuel vaporizing section 32, into which fuel is sprayed by the output ports 46 of the fuel injectors 38. Ambient air is also introduced into the preliminary mixing chamber 44 through an ambient air conduit 50 and is to be mixed with fuel sprayed by the fuel injectors 38. The preliminary mixing chamber 44 is defined in part by an exterior surface 52 of a vortex chamber housing 54 and the exterior surface 68 of a tapered extension 58. The preliminary mixing chamber 44 is further defined by the interior surface 56 of a pressure differential supply jacket 60. The purpose and function of the jacket 60 and the vortex chamber housing 54 are discussed in more detail below.

The vortex chamber housing 54 comprises the exterior surface 52, an inner chamber wall surface 62, and a bottom surface 63. Additionally, the vortex chamber housing 54 includes the tapered extension 58 to enhance the flow of fluid in the preliminary mixing chamber 44, and is to be secured to the injector plate 42 by set screw 48 (FIG. 3) inserted through bore 49. The vortex chamber inner chamber wall surface 62 defines a vortex chamber 64 in which a vortical flow of fluid is created. The vortex chamber housing 54 has an array of apertures 66 journalled into the housing at an angle to allow the input of fluid, such as an air/fuel mixture, tangentially into the vortex chamber 64. A vortex chamber top edge 61 abuts a jacket top inside surface 55. Advantageously, a conventional gasket (not shown) may be interposed between the edge 61 and the top surface 55 to prevent fluid from leaking into the vortex chamber 64 between the edge 61 and the surface 55.

Figure 3:
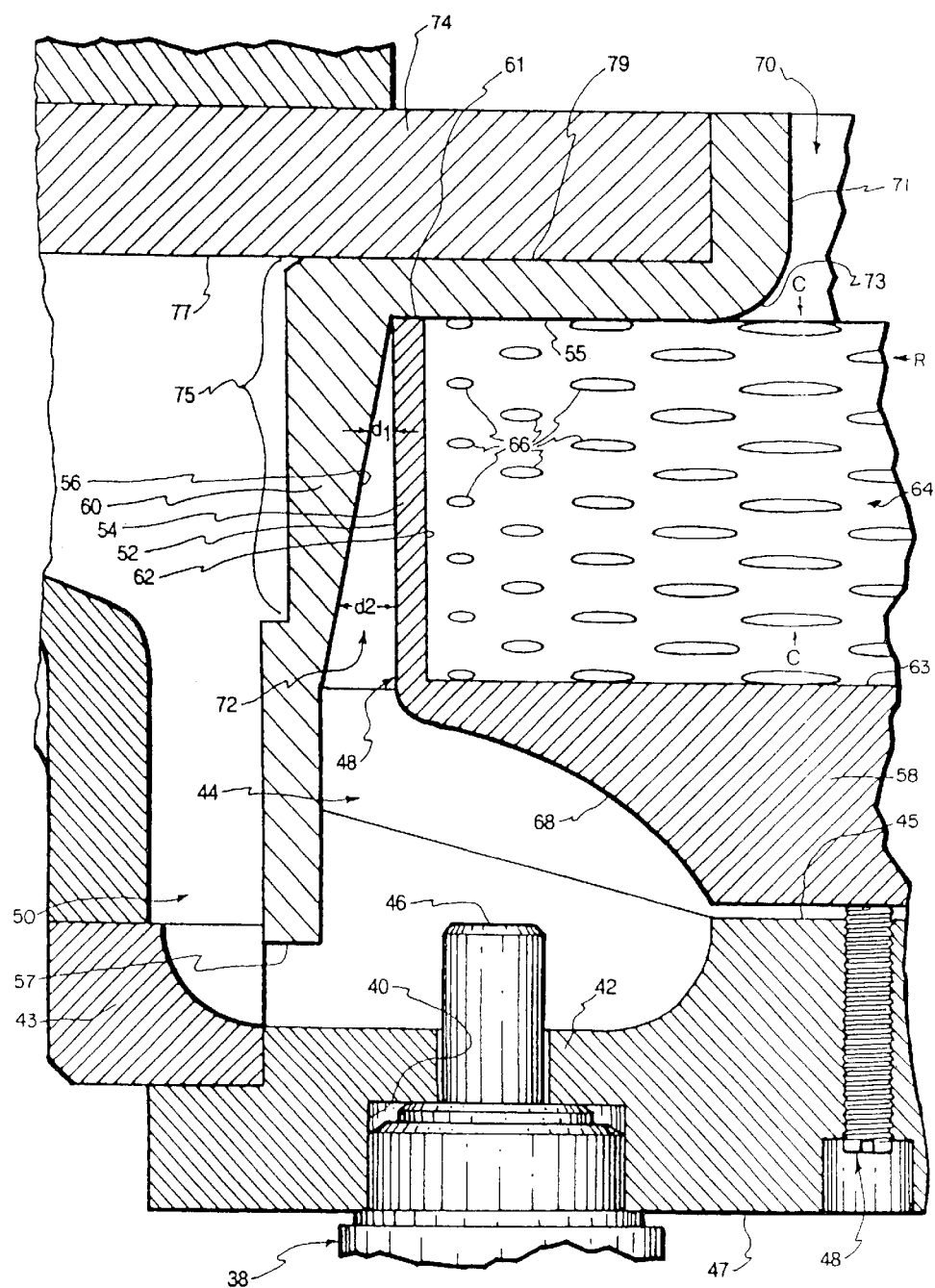
FIG. 3 is an enlarged breakaway sectional view of a portion of the vaporizing section of FIG. 1.

As shown in FIG. 3, the array of apertures 66 are arranged in a plurality of rows R and in a plurality of columns C about the vortex chamber 64 to enhance the turbulence of the vortical flow through the chamber 64. Preferably, the rows R and the columns C are circumferentially staggered or offset relative to each other. By orienting the array of apertures 66 in staggered rows and columns, the tendency for the fluid within the vortex chamber 64 to separate into discrete orbital rings is eliminated or at least substantially alleviated. Additionally, this aperture orientation significantly enhances the degree of turbulence (and thus the efficiency of vaporization) within a given vortex chamber.

A pressure differential supply configuration is formed by a tapered jacket 60 positioned around the vortex chamber housing 54. As shown, the jacket 60 includes a variable thickness portion 75 which provides an increasing diameter to the tapered inside surface 56. The jacket 60 terminates at edge 57. The jacket 60 also includes an output port 70 through which fluid flows after being processed in the vortex chamber 64. The output port 70 is defined by a cylindrical surface 71 which intersects the jacket top surface 55 at rounded corner 73. The diameter of the jacket interior surface 56 is illustrated as being smallest at the end closest to the jacket output port 70. The diameter of the jacket interior surface 56 gradually increases from that point toward the edge 57. While the variable diameter surface is illustrated as generally comprising the tapered inside surface 56, it is appreciated that a stepped inside surface may also be effectively employed.

The variable diameter jacket interior surface 56, when positioned around the vortex chamber housing 54, defines a variable width gap 72 between the jacket interior surface 56 and the vortex chamber housing exterior surface 52. As shown in FIG. 3, the variable width gap has a smaller width at $d_1$ and a larger width at $d_2$. The variable width gap 72 creates a variable pressure differential across the apertures 66 formed in the vortex chamber housing 54 and restricts the flow through the apertures 66 closer to the port 70 more than the apertures 66 located farther from the port 70. Thus, a differential pressure of fluid is provided at the various input apertures 66 according to the location of the apertures relative to the jacket output port 70. In operation, the apertures 66 closest to output port 70 will be provided with more pressure because this end comprises the lower pressure end of the fuel vaporizing section 32.

By positioning a variable pressure supply configuration, such as the jacket 60, around the apertures 66 formed in the chamber housing 54, the amount of fluid flow entering the various apertures 66 is substantially equalized. Having a substantially equalized flow of fluid through the various apertures 66 enhances the efficiency and effectiveness of the vortex chamber 64.

The jacket 60 and the vortex chamber housing 54 are illustrated in FIG. 1 as being mounted within a fuel vaporizing housing 74 having an interior surface 76. Specifically, a top outside surface 79 (FIG. 3) of the jacket 60 is positioned adjacent to a top inside surface 77 of the housing 74. The ambient air conduit 50, discussed above, is defined by the fuel vaporizing housing interior surface 76 and the exterior surface 68 of the tapered extension 58.

Figure 4:
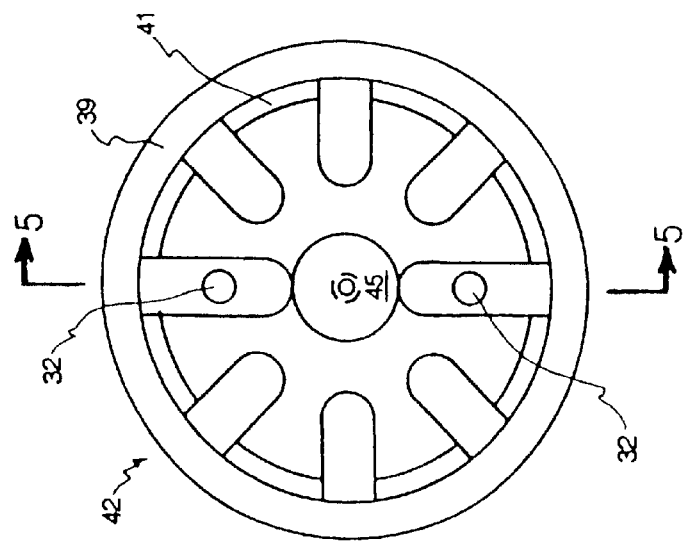
FIG. 4 is a top view of the injector plate of FIG. 1.
Figure 5:
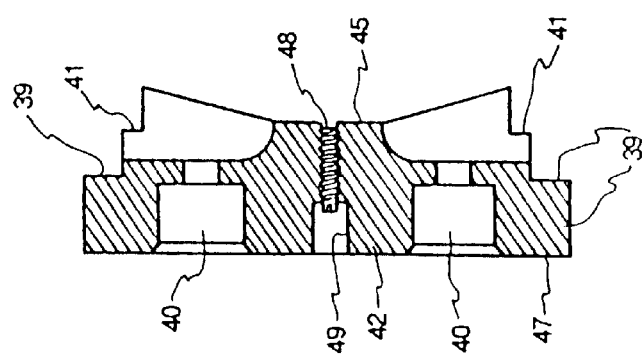
FIG. 5 is a sectional view taken along line 5—5 of FIG. 4 of the injector plate.
Figure 6:
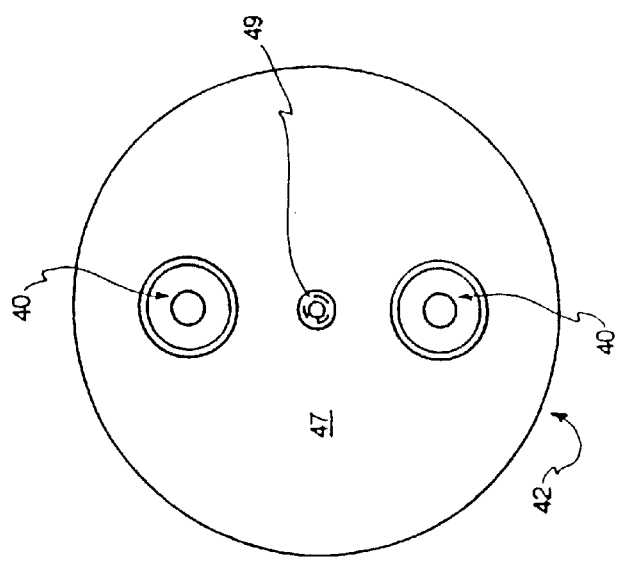
FIG. 6 is a bottom view of the injector plate of FIG. 1.

The injector plate 42 is shown in FIGS. 1, 3, 4, 5, and 6. The injector plate 42 includes a pair of bores 40 formed through the bottom surface 47 to receive the fuel injectors 38 (FIG. 1). The injector plate 42 further includes a first shoulder 39 and a second shoulder 41 (FIGS. 4 and 5). The first shoulder 39 abuts a connecting member 43 and the second shoulder 41 abuts the jacket edge 57 (FIG. 1). A cylindrical center extension 45 abuts and is connected to the tapered extension 58 (FIG. 1) via the set screw 48.

Figure 2:
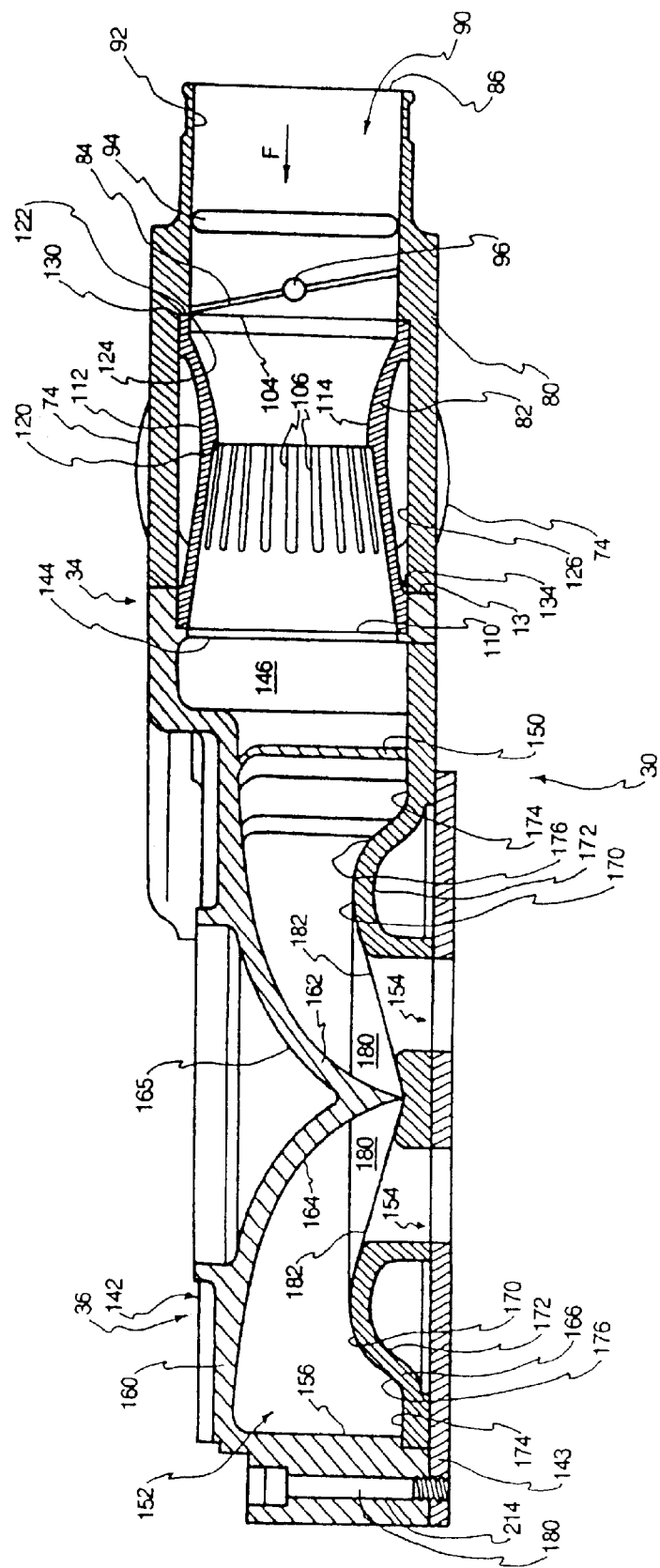
FIG. 2 is a side sectional view taken along line 2—2 of FIG. 1, of the centrifugal vortex system.

The main air section 34, as illustrated in FIGS. 1 and 2, comprises a main air housing 80, a venturi body 82, and a conventional butterfly throttle plate 84. An air intake opening 86 is positioned at one end of the main air section 34. The air intake opening 86 leads to an interior cylindrical portion 90 having an annular inside surface 92.

The conventional throttle plate 84 is pivotally secured within the interior cylindrical portion 90. The throttle plate 84 is secured to a rotatable central shaft 96, which is oriented transverse to the direction of air flow F through the hollow interior 90. Rotation of the shaft 96 will adjust an inclination angle of the throttle plate 84 within the hollow interior 90, thereby changing the volume of air and thus the air/fuel mixture admitted to the engine.

An ambient air channel 100 is formed in the main air intake housing 80. The air channel 100 is in fluid communication with a slot 94 formed in the main air intake housing 80. Sequential ambient air conduits 102 and 50 allow air to pass through the channel 100 and the slot 94 into the preliminary mixing chamber 44.

A venturi 82 is mounted within the main air section 34 and comprises an input 104, a plurality of elongated apertures 106, and a venturi output 110. Additionally, the venturi 82 includes a venturi exterior surface 112 and a venturi interior surface 114. As shown, the diameter of the venturi interior surface 114 is maximized at the venturi input 104 and at the venturi output 110. The diameter of the venturi interior surface 114 is approximately the same at the venturi input 104 and at the venturi output 110. In contrast, the diameter of the venturi interior surface 114 is minimized at the venturi throat 116. An annular step is formed on the venturi interior surface 114 adjacent to the venturi throat 116.

The main air intake section 34 also includes a transverse annular edge 122 (FIGS. 1 and 2) which intersects the annular inside surface 92 at an annular outside corner 124. The edge 122 also intersects an annular surface 126 at an annular inside corner 130. The annular surface 126 also intersects with a transverse edge 132 at an annular corner 134. The venturi 82 is positioned within the main air section adjacent to the annular surface 126 by securing the exterior surface 112 of the venturi 82 to the annular surface 126 by adhesion, by an interference fit, or by any other conventional manner.

An intermediate mixing chamber 136 (FIG. 1) is formed in the main air intake section 34 to cause a spinning column of fluid exiting the jacket output port 70 to enfold and to mix turbulently prior to entering the venturi 82 through the elongated apertures 106. The intermediate mixing chamber 136 serves to further vaporize and homogenize the fluid. The intermediate mixing chamber is defined by the annular surface 126 and the transverse annular surface 140 which intersect at corner 142. The centrifuge section 36 is attached to the main air section 34 at the transverse edge 132.

Fluid discharged from the venturi output 110 passes into the centrifuge section 36 through an intake opening 144. The centrifuge section 36 generally comprises a centrifuge housing 142, the intake opening 144, an entry chamber 146, a series of baffles 150 oriented tangentially relative to a centrifuge chamber 152, and a plurality of output passageways 154. As shown, the centrifuge housing is a generally cylindrical configuration comprising an annular vertically directed wall surface 156 which is interrupted by the intake opening 144. The wall surface 156 is formed integrally with a top wall 160 (FIG. 2).

As shown in FIG. 2, a hub portion 162 extends down from the centrifuge top wall 160. The hub portion 162 has an inner surface 164 and an exterior surface 165, both of which are shown as being substantially parabolic in shape. As discussed in further detail below, the hub portion 162 substantially reduces the volume of the centrifuge chamber 152 and enhances the circular, centrifugal flow of fluid about the hub portion within the centrifuge chamber 152.

Opposite the top wall 160, a contoured bottom insert 166 is positioned within the centrifuge chamber 152. The contoured bottom insert 166 comprises a contoured top surface 170 and a contoured bottom surface 172. The contoured top surface has an annular flat portion 174, an upward directed curved portion 176, and a conically shaped central portion 180. As shown, each output 154 includes an output opening 182 formed in the conically shaped portion 180.

As mentioned above, the centrifuge 136 also includes the series of tangentially oriented baffles 150 positioned within the entry chamber 146. Each baffle 150 comprises leading edge 184, and an intermediate corner 186 as well as a rounded trailing end 190. A leading flat surface 192 is formed between the leading edge 184 and the corner 186. A flat surface 194 is formed between the leading edge 184 and the trailing end 190. Lastly, a surface 196 is formed between the corner 186 and the trailing end 190.

The baffles 150 are aligned relative to one another so as to create a plurality of tangential fluid flow passageways 200 formed between the surfaces of adjacent baffles 150. Additionally, a tangential passageway 202 is formed between the surface 194 of a baffle 150 adjacent to the vertically oriented wall 206 of the entry chamber 146. Moreover, a tangential passageway 204 is formed between the surface 192 of a baffle adjacent to a vertical wall 210 of the entry chamber 146.

As shown in FIG. 1, each trailing flat surface 194 is oriented at a tangential angle relative to the annular wall 156 of the centrifuge section 36. Accordingly, the flow of fluid introduced into the centrifuge chamber 152 through the passageways 200, 202, and 204 is introduced in a direction substantially tangent to the annular wall 156 to enhance the circular and centrifugal flow of fluid in the chamber 152.

To secure the centrifuge housing 142 to an engine manifold (not shown), mounting locations 212, 214, and 216 are formed in the centrifuge housing to permit fasteners, such as bolts 180 (FIG. 2) to secure the centrifuge housing 142 to the engine via an interface plate 143.

Figure 7:
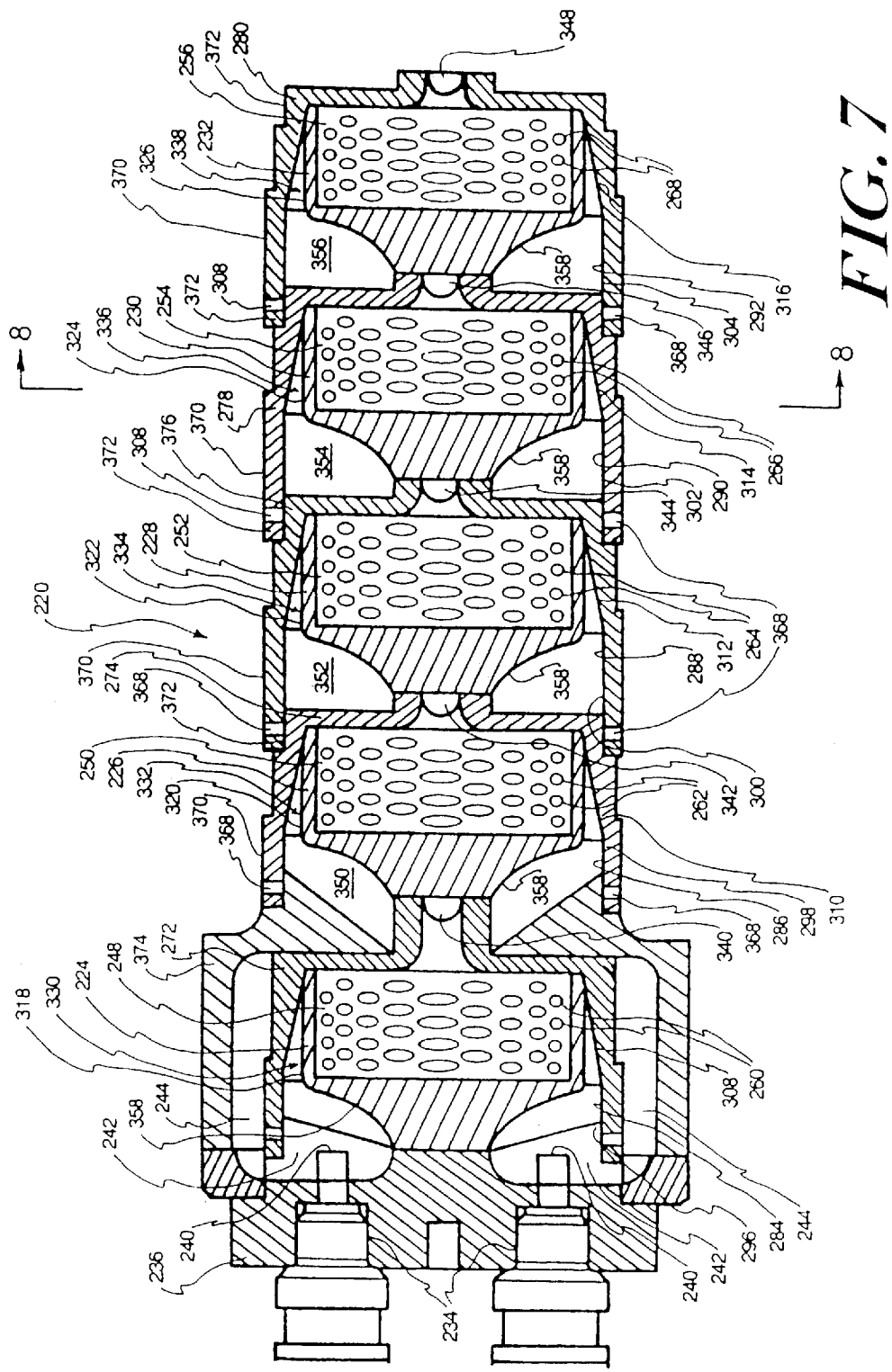
FIG. 7 is a sectional side view of an alternative embodiment of a vortex configuration according to the present invention.

FIG. 7 illustrates an alternative embodiment of the present invention. This embodiment shows a vortex chamber assembly 220 which generally comprises conventional electronic fuel injectors 222, a first vortex chamber housing 224, and subsequent vortex chamber housings 226, 228, 230, and 232. In this configuration, the chamber housings 226–232 each receive a flow of fluid exclusively from the preceding chamber housing. For example, the chamber housing 228 receives fluid exclusively from the output of chamber housing 226 and so on.

The fuel injectors 222 are mounted within bores 234 formed in an injector plate 236. Each fuel injector includes an output port 240 which sprays fuel into a preliminary mixing chamber 242. Ambient air is introduced into the preliminary mixing chamber 242 via an ambient air conduit 244. The preliminary mixing chamber 242 and the ambient air conduit 244 are configured and function in a manner similar to the configuration and function of the preliminary mixing chamber 44 and the ambient air conduit 50 illustrated in FIG. 1.

The chamber housings 224, 226, 228, 230, and 232 respectively define vortex chambers 248, 250, 252, 254, and 256. The vortex chambers 224–232 each have an array of apertures 260–268. Each array of apertures 260–268 are arranged in a plurality of rows and a plurality of columns in a manner similar to that illustrated in FIG. 3. Moreover, each array of apertures 260–268 are arranged in a staggered configuration so as to enhance the turbulence of a vertical flow through the respective vortex chamber 248–256.

Pressure differential supply inlets are formed by tapered jackets 272, 274, 276, 278, and 280 positioned about the chamber housings 224, 226, 228, 230, and 232, respectively. Each functions in a manner similar to the jacket 60 described in connection with FIG. 1. Each of the jackets 272–280 has a respective interior surface 284, 286, 288, 290, 292. The jacket interior surfaces 284–292 each comprises a constant diameter portion 296, 298, 300, 302, 304, respectively, and a variable diameter interior surface portion 308, 310, 312, 314, 316, respectively. Each chamber housing 224, 226, 228, 230, 232 has a respective exterior surface portion 318, 320, 322, 324, 326. The jackets form variably sized gaps 330, 332, 334, 336, 338 between the surfaces 330–338 and the surfaces 308–316, respectively. As such, the variable spaced gaps allow a differential pressure of fluid at the various apertures 260–268 according to the location of the apertures 260–268 and function in a manner similar to the gap 72 (FIGS. 1 and 2).

Figure 10:
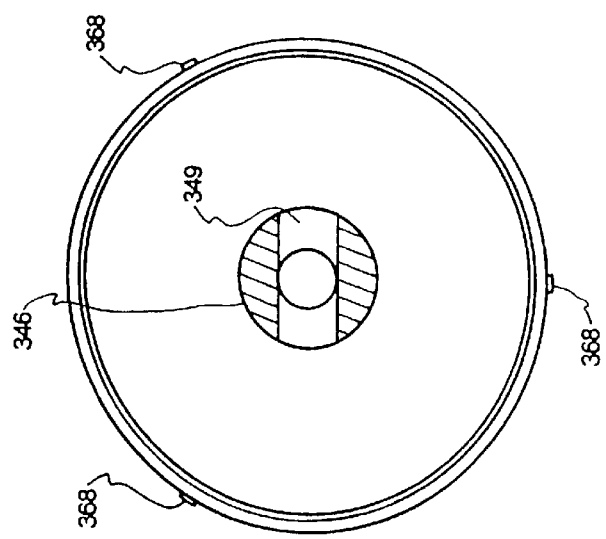
FIG. 10 is a top view of the differential inlet supply configuration to a vortex housing assembly of FIG. 8.
Figure 9:
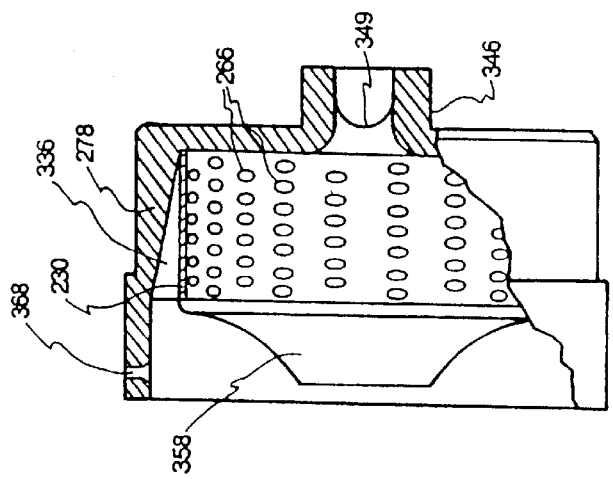
FIG. 9 is a side sectional view taken along line 9—9 of FIG. 8 of the differential inlet supply configuration to a vortex housing assembly.
Figure 8:
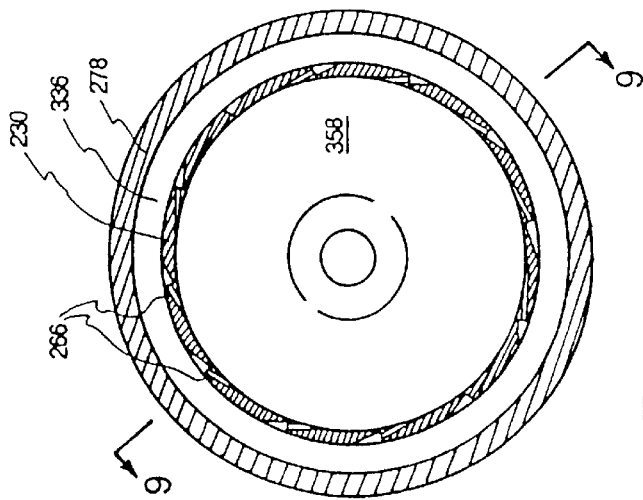
FIG. 8 is a bottom sectional view taken along line 8—8 of FIG. 7 of the differential inlet supply configuration to a vortex chamber assembly.

Additionally, each jacket 272–280 has a respective output port 340–348 which is in fluid communication with the subsequent vortex chamber. FIGS. 8–10 illustrate the jacket 278 vortex chamber 254 in greater detail. Each of the output ports 340–348 is in the form of a U-shaped slot represented by reference numeral 349 in FIGS. 9 and 10. The output ports 340–346 are in fluid communication with subsequent mixing chambers 350, 352, 354, and 356, respectively, so that the apertures 262–268 receive a fluid mixture exclusively from the output ports 340–346 to maintain a substantially constant air second fluid mixture as no additional air is introduced into the fluid stream as the fluid stream passes through the vortex chambers 250–256. Moreover, to enhance the mixing and vortical nature of the flow through the mixing chambers 242, 350, 352, 254, and 356, each chamber housing 224–232 has a conically tapered base portion 358.

Apertures 368 are formed in the jackets 274–280 for receiving fasteners (not shown), such as conventional set screws, to secure the jacket lower portions 370 to a preceding jacket's upper portion 372 or to a vaporizing housing 374.

Figure 13:
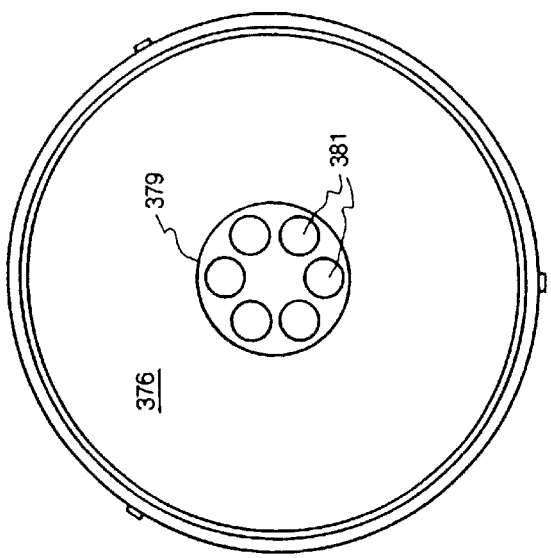
FIG. 13 is a top view of the differential inlet supply configuration for the vortex chamber assembly of FIG. 11.
Figure 12:
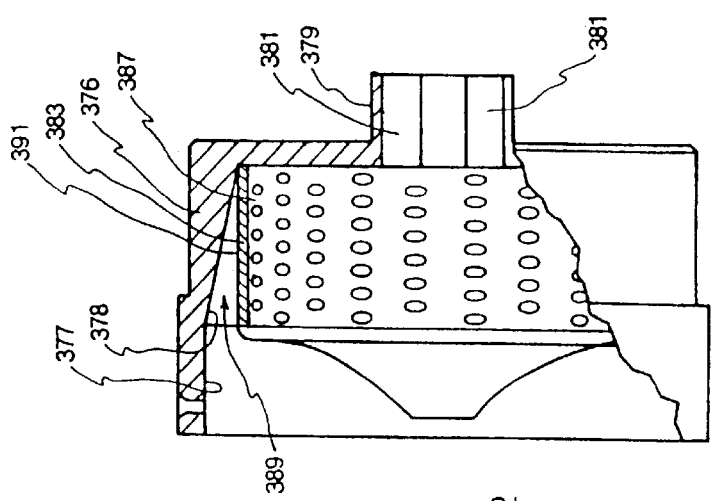
FIG. 12 is a side sectional view, taken along line 12—12 of FIG. 11, of the differential inlet supply configuration to a vortex chamber assembly.
Figure 11:
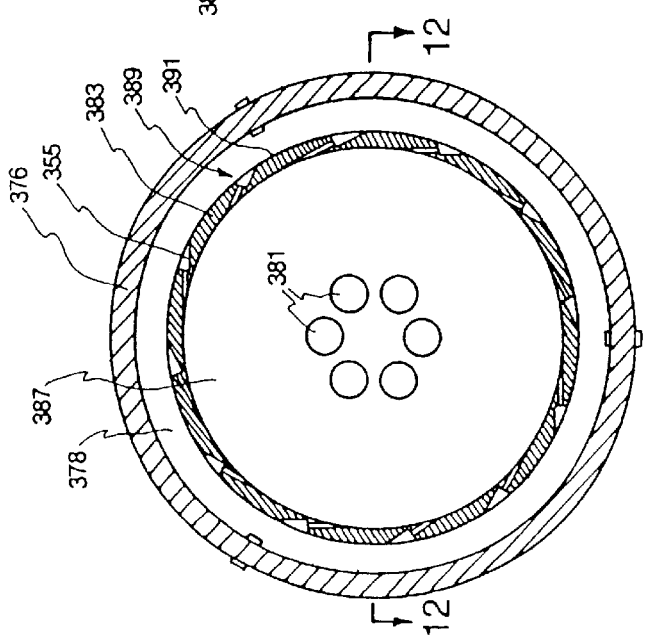
FIG. 11 is a bottom sectional view of an alternative embodiment of a differential inlet supply configuration to a vortex chamber assembly according to the present invention.

FIGS. 11–13 illustrate an alternate embodiment of a jacket-chamber assembly for use in a plurality of vortex chamber configurations such as that illustrated in FIG. 7. Specifically, a jacket 376 is illustrated as having a constant diameter inside surface 377, a variable diameter inside surface 378, an output port 379, and output apertures 381. The chamber housing 383 is shown as having a plurality of apertures 385 formed at an angle therein and leading tangentially into a vortex chamber 387. A variably spaced gap 389 is formed between the interior surface 378 of housing 376 and the exterior surface 391 of the vortex chamber 383.

FIG. 14 shows another alternative embodiment of a vortex chamber according to the present invention. A chamber housing 380 having an exterior surface 382 and an inner chamber wall 384 defines a vortex chamber 386. To increase the turbulence of a vortical flow within the chamber 386, and to break down into smaller particles any non-vaporized particles in the vortical flow, steps 388 are formed on the inner chamber wall 384. As shown, each step 388 comprises a ramp surface 390 and a transverse surface 392. A plurality of apertures ramp 394 are formed in the housing 380 and intersect the inner chamber wall 384 at transverse surfaces 392. As a fluid flows through the vortex chamber 386, the steps 388 cause relatively small eddies to be created adjacent to the various transverse surfaces 392 which enhances the turbulence of the flow through the chamber 386.

As an alternative or additional manner of increasing the turbulence of a vortical flow within the chamber 386, and to break down into smaller particles any non-vaporized particles in the vortical flow as well as enhance the vaporization of the non-vaporized particles, the inner chamber wall 384 may comprise a textured surface. The textured or irregular surface may be formed by heavy grit sand blasting or applying a type of glass beading. A textured or irregular inner chamber wall surface will tend to cause fluid to flow through the chamber 386 in a more turbulent manner. When non-vaporized particles collide with the textured inner chamber wall surface, the non-vaporized particles will spread apart, break down into smaller particles, and vaporize more readily as compared to a smooth inner wall surface.

FIGS. 15–17 illustrate yet another alternative embodiment of a vortex assembly according to the present invention. As shown in FIG. 15, a centrifugal vortex system 400 generally comprises a fuel vaporizing section 402 in fluid communication with a main air section 404. The main air section 404 is in fluid communication with a centrifuge section 406. The fuel vaporizing section 402 includes a main air housing 410 which has inside surface 412. The inside surface 412 defines a main air chamber 414 into which ambient air is introduced. A base plate 416 is attached to the main air housing 410 along a main air housing edge 418. An injector plate 420 is secured within the base plate 416 by base plate extensions 422. Fuel injectors 424 (only one is shown in FIG. 15—the other fuel injector positioned directly behind the illustrated fuel injector 424) are secured within the injector plate 20 for spraying fuel into a first vortex chamber 426 formed in the chamber housing 428. Also formed in the chamber housing 428 are second vortex chamber 430, third vortex chamber 432, and fourth vortex chamber 434.

To permit air to enter the vortex chambers 426, 430, 432, and 434, a plurality of apertures 436 (FIGS. 16 and 17) are formed at an angle in the chamber housing 428 so that the apertures enter into each vortex chamber tangentially. Each aperture is oriented substantially tangentially to inner surfaces 438–444 to permit air to be tangentially introduced into each vortex chamber 428, 430, 432, and 434. The apertures are preferably formed in an array of rows and columns, the columns being offset relative to each adjacent row.

To enhance the turbulence, pressure differentials, shear forces, and changes in velocity applied to the fluid as it passes through the chambers 428–434, the array of apertures 436 are advantageously oriented in opposite tangential directions in adjacent chambers. For example, the apertures in the chamber 428 are oriented to introduce fluid in a first vortical flow direction within the chamber 428 and the apertures in the chamber 430 are oriented in a direction opposite to the orientation of the apertures in chamber 428 to introduce fluid in a second vortical flow direction within chamber 430.

A pressure differential supply configuration formed by a tapered jacket 450, is provided around the outside of the series of vortex chambers. The jacket 450 is secured to an end 452 of the vortex chamber housing 428. The jacket 450 generally comprises a tapered portion 454 and an elongated tube portion 456. The jacket portion 454 is configured and operates in a manner substantially similar to the manner of operation of jacket 60 (FIG. 1) and comprises an exterior surface 458 and a variable diameter inner surface 460 to form a variable width gap 462 between the inner surface 460 and the exterior surface 464.

The variably width gap 462 creates a varying degree of pressure resistance across the apertures 436 formed in the chamber housing 428. Where the gap is more narrow toward the downstream end 452 of the chamber housing, the fluid pressure is maximized. Fluid pressure decreases from that point in an upstream direction toward chambers 432, 430, and 428. In this configuration, the pressure resistance across the apertures 436 varies according to the location of a given aperture. The jacket 450 also includes an output boss 470 which comprises an annular boss exterior surface 472 and an annular boss interior surface 474. The purpose and function of the jacket output boss is described below.

The tube portion 456 of the jacket 450 comprises an inner surface 466 and an exterior surface 468. The interior surface 466 defines a tube hollow interior 470. A helically wound solenoid 476 is secured around the tube portion 456 of the jacket 450 for selectively creating a magnetic field within the tube interior. An elongated conduit 478 formed integrally with a conduit base 480 is slidingly positioned within the jacket tube portion 456 to permit the conduit base 480 to travel within the tube portion 456 between the positions illustrated in FIGS. 16 and 17. A biasing member, such as a spring 482, is also disposed within the jacket tube portion 456 between the conduit base 480 and the jacket portion 454. The spring 482 selectively maintains the conduit base 480 in the position illustrated in FIG. 17.

As shown in FIG. 17, when the solenoid 476 is not energized, the elongated conduit 478 is withdrawn from the vortex chambers 428–434. The activation of the solenoid 476 causes the conduit base 480 to move into the position illustrated in FIG. 16, thus compressing the spring and advancing the elongated conduit 478 through the chamber outputs 484, 486, and 488 into direct communication with chamber output 490. Activating the solenoid 476 and causing it to move the elongated conduit 478 into the position illustrated in FIGS. 15 and 16, causes the vortical flow through the housing 427 to be isolated in the vortex chamber 428 and permits the flow to selectively bypass the remaining chambers 430, 432, and 434.

Advantageously, the elongated conduit 478 is selectively, and briefly, moved into position illustrated in FIGS. 15 and 16 for intervals on the order of 0.5 seconds during transient periods of engine acceleration and deceleration. By selectively isolating the chamber 428 during these periods, a well-known problem of "acceleration stumble" is substantially alleviated.

The problem of acceleration stumble generally occurs during transient periods of acceleration and deceleration. For example, with respect to FIG. 15, during periods of acceleration, the throttle plate 518 opens and thus causes the pressure in the main air chamber 414 to drop. This drop in pressure, in turn, causes a decrease in the amount of air entering into the vortex chambers 426, 430, 432, and 434. With less air entering the vortex chambers, a smaller portion of the fuel sprayed from the fuel injector 424 is carried through the vortex chambers and into the engine, thus causing a relatively lean fuel mixture. Because the fuel during this period is not effectively passing through the vortex chambers, an amount of fuel accumulates in the vortex chambers 426 and 430. Then, as the accumulated fuel passes through the remaining vortex chambers, a fuel-rich mixture is provided to the combustion engine (not shown). This period of fuel-lean fluid followed by the period of fuel-rich fluid and the associated engine difficulties associated with these drastically varying air-fuel ratios, is referred to as "acceleration stumble."

Additionally, by employing the elongated conduit 478 as described above, the amount of hydrocarbons in the fluid is greatly decreased. Moreover, bypassing chambers 430–434 during acceleration and deceleration will prevent chambers 430–434 from dominating the chamber 428.

The main air intake section 404, as illustrated in FIG. 15 includes a cylindrical air intake 500. An annular channel 502 is formed on the air intake port to facilitate the attachment of a conventional ambient air conduit (not shown). The air intake port 500 also introduces air into an ambient air conduit 508 formed in an intermediate housing 510. As shown, the intermediate housing 510 is rigidly attached to the main air housing 410 and also includes concentric bores 512 and 514. The downstream end 518 of the jacket tube portion 456 is secured within the bore 512 to permit fluid discharged from the downstream end 518 to be passed from the jacket tube portion 456 through the bore 514 into the main air intake section 404.

To regulate the volume of air admitted to the engine (not shown), a conventional throttle plate 518 is secured to a rotatable central shaft 520, which is oriented transverse to the direction of air flow through the main air section 404.

The venturi 506 comprises a large diameter air intake opening 522, a narrow throat portion 524, and a large diameter air/fuel mixture output opening 526. The venturi 506 further comprises a venturi exterior surface 528 and a venturi interior surface 530. The diameter of the venturi interior surface 530 is minimized at the venturi narrow throat 524 and maximized at the intake and output openings 522 and 526. The venturi output opening 526 is in direct communication with a main air section output channel 532 for discharging fluid from the main air intake section 404 into the centrifuge 406.

The centrifuge 406 comprises a generally cylindrical configuration. The centrifuge includes an annular wall 534 having an exterior surface 536 and an interior surface 538. The wall 534 is interrupted by an intake opening 540 for receiving fluid from the output channel 532 of the venturi into a centrifuge chamber 542. The centrifuge chamber 542 is further defined by a centrifuge top plate 544 and a centrifuge bottom plate 546.

A large diameter output aperture 548 is formed in the centrifuge bottom plate 546 for discharging fluid from the centrifuge chamber 542. The output aperture 548 is defined by a rounded surface 550 having a minimum diameter 552 and a maximum diameter 554.

To enhance the vacuum pressure at the output aperture 548, the ratio of the diameter of the venturi inside surface 530 at the throat 524 to the minimum diameter 552 is greater than 1.58:1, preferably approximately 1.66:1.

The centrifuge housing 406 is securable to an engine (not shown), via apertures 558 formed in mounting flanges 556 extending from wall 534.

FIG. 18 illustrates still another alternative embodiment of a vortex chamber assembly according to the present invention. A chamber housing 570 comprises an exterior surface 572 and interior surfaces 574, 576, 578, 580, and 582. The interior surfaces 574–582 are each substantially cylindrical and define, respectively, vortex chambers 584, 586, 588, 590, and 592.

Apertures 594 are formed tangentially, in an array with offset columns and rows, in the chamber housing 570 to allow the input of fluid tangentially into each vortex chamber 584–592. This tangential input of fluid creates a turbulent vortical flow of fluid through the vortex chambers which breaks down the fluid into smaller particles and vaporizes remaining liquid particles in the vortical flow. The apertures 594, as shown, are arranged in a plurality of rows and in a plurality of columns, preferably staggered relative to one another, to further enhance the turbulent nature of the flow through the chambers 584–592.

A cylindrical output flange 596 comprises an exterior surface 598 and an interior surface 600. The output flange is attached to an upstream end 602 of the chamber housing 570. The interior surface 600 defines the output from vortex chamber 584 of the vortex chamber housing 570. As illustrated, the vortex chambers 584–592 have sequentially decreasing diameters. That is, the diameter of the inside surface 582 is smaller than the diameter of inside surface 580, which is, in turn, smaller than the inside surface of surface 576, which is smaller than the inside surface 574. Given this configuration, as the fluid passes through the chambers 584–592 in a vortical flow having a low pressure end at the output 604 and a high pressure end adjacent to an upstream end 606, the tendency for the chambers closest to the low pressure end (chambers 584 and 586) to receive more flow through the apertures 594 than the chambers closest to the high pressure end 604 (chambers 590 and 592) is significantly reduced.

Additionally, to enhance the vaporization of a fluid as it passes through the chambers 584–592, appropriately sized nozzles 608 (FIG. 18) are positioned at an upstream end of each of the chambers 584, 586, 588, and 590, respectively. The nozzles 608 cause the fluid passing through the vortex chambers to be subjected to additional pressure differentials, thus enhancing the vaporization and break down of fluid particles. The nozzles 608 are preferably sized so as to be secured within the upstream end of the chambers 584–590 by a press-fit attachment.

FIG. 19 discloses a yet additional embodiment of the present invention. As shown, FIG. 19 discloses a vortex configuration 611 comprising a chamber housing 612 having an exterior surface 614 and interior surfaces 616, 618, 620, 622, and 624. The internal surfaces 616–624 are substantially cylindrical and respectively define vortex chambers 626, 628, 630, 632, and 634. Apertures 636 are formed tangentially relative to interior surfaces 616–624 of the vortex chambers 626–634. The apertures 636 are formed in an array in the chamber housing 612 to allow the input of fluid tangentially into the vortex chambers 626–634. This tangential input of fluid creates a vortical flow through the vortex chambers for breaking down into smaller particles and further vaporizing or homogenizing liquid particles in the vortical flow.

A cylindrical output flange 640 is attached to an end 642 of the chamber housing 612. The output flange 640 comprises an interior surface 644 and an exterior surface 646. An output port 648 is defined by the output flange interior surface 644. The output flange 640 is similar to the output flange 596 (FIG. 17) except that the diameter of the inside surface 644 is smaller than that of the inside diameter 600 (FIG. 17). Additionally, the output flange 640 includes an aperture 650, through which a screw (not shown) can be selectively inserted as a way to adjust the flow resistance through the output member 640. The more the screw is advanced into the output port 648, the more air resistance is imparted to the vortical flow as the vortical flow passes through the output port 648.

In general, the air resistance through a vortex configuration can be varied by changing the diameter of the output aperture and/or changing the diameter of the passageways between adjacent vortex chambers within the vortex configuration. The embodiment of FIG. 18 shows a relatively large output and relatively small passageways between adjacent vortex chambers due to the nozzles 608. Conversely, the embodiment of FIG. 19 shows a smaller output and larger passageways between chambers. In some applications it has been found that the embodiment illustrated in FIG. 19 is preferable to the embodiment of FIG. 18.

Figure 20:
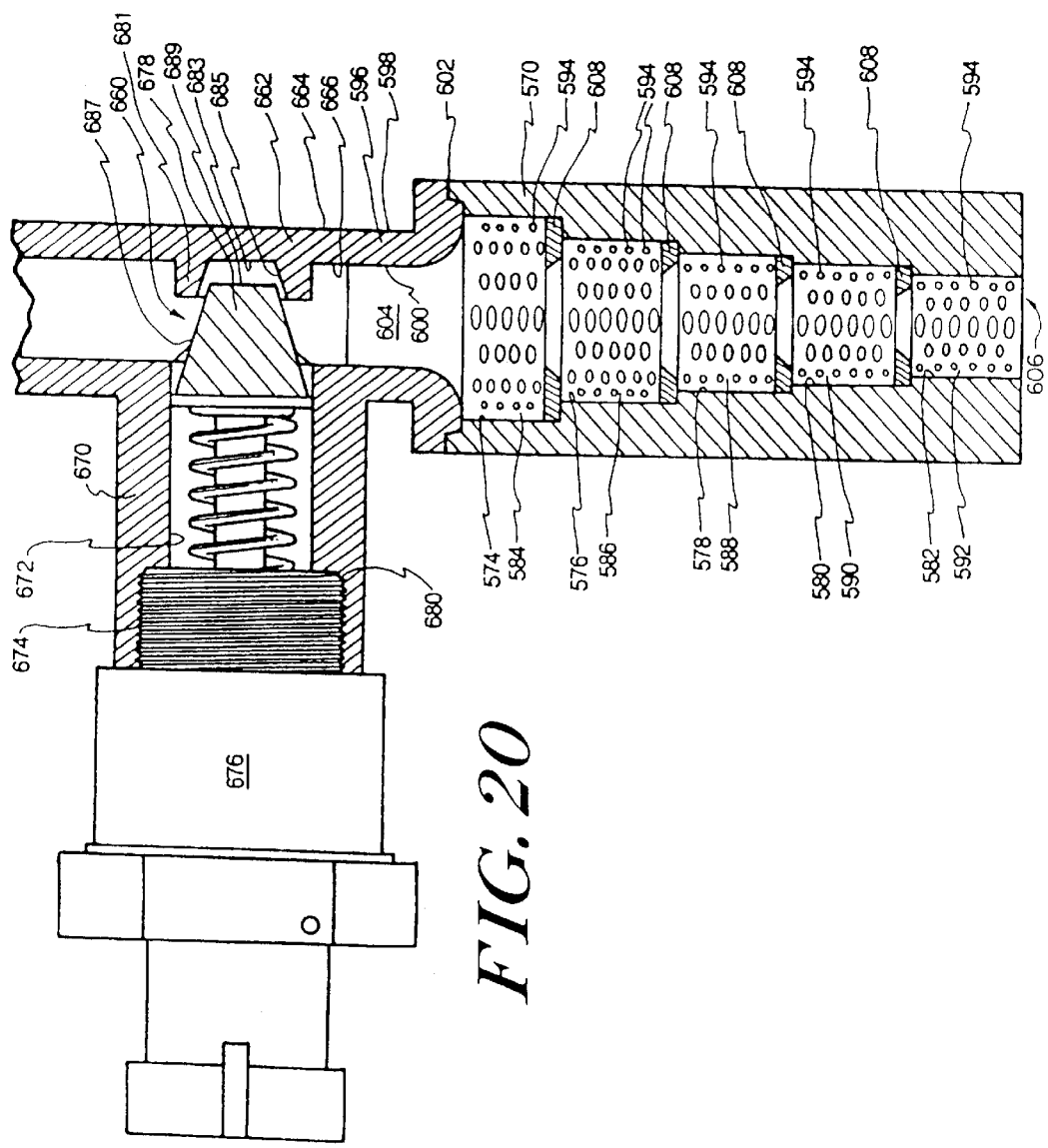
FIG. 20 is a partial sectional view of an adjustable cross-sectional area output port mechanism according to the present invention.

FIG. 20 illustrates a yet additional embodiment of the present invention. Specifically, FIG. 20 illustrates the chamber housing 570 of FIG. 18 in combination with an adjustable cross-sectional area output port 660 formed in an output housing 662. As shown, the output housing 662 comprises an outside surface 664, an inside surface 666 and is positioned adjacent to the output 604 of the chamber housing 570. The inside surface 666 defines the output port 660 into which fluid flows from the output 604.

The housing 662 also comprises an actuator mounting extension 670. The mounting extension 670 comprises a cylindrical inside surface 672 and a threaded inside surface 674. An actuator, such as a stepper motor 676, comprises a male threaded portion 680 which is securable to the corresponding female threaded portion 674 of the actuator housing 670.

The stepper motor 676 acts as a linear actuator to move a conical block 678 relative to a conical seat 681 formed in the conduit 668. The conical seat 681 comprises a flat bottom surface 683 and a conically shaped side surface 685. The side surface 685 is sized to engage a side surface 687 of the block 678 when a conical block end surface 689 contacts the conical seat bottom surface 683.

Accordingly, by selectively moving the conical block 678 relative to the seat 681, the effective cross-sectional area of the passageway formed by interior surface 666 may be selectively varied. Advantageously, the cross-sectional area of the conduit 668 may be increased or decreased, depending on the desired output. Moreover, the air resistance through the output port 660 may be varied by moving the conical block 678 relative to the seat 681.

Figure 21:
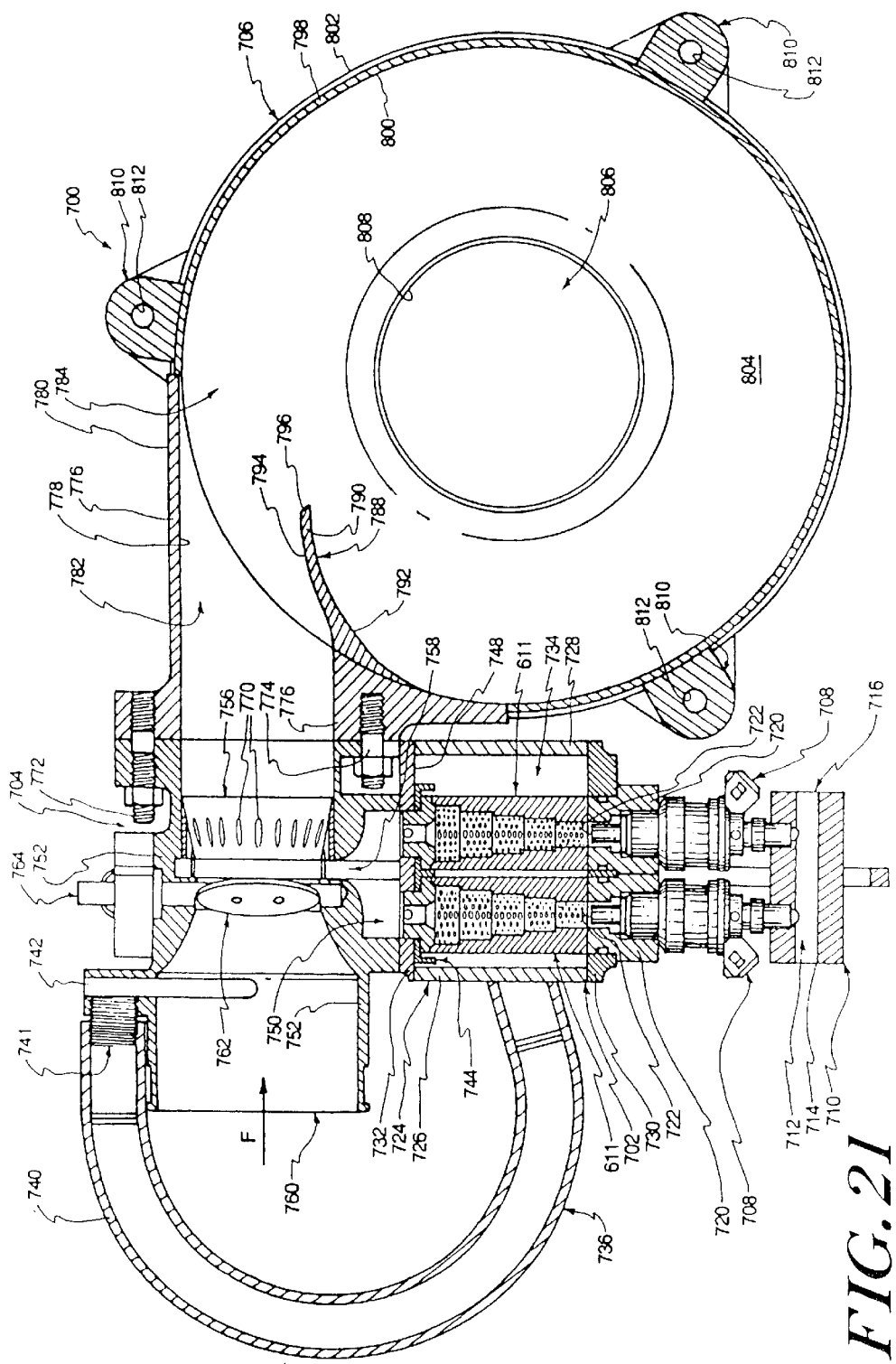
FIG. 21 is a top sectional view of an alternative embodiment of a centrifugal vortex system according to the present invention.

FIG. 21 shows another alternate embodiment of the present invention. This embodiment shows a centrifugal vortex system 700 comprising a fuel vaporizing section 702, a main air section 704, and a centrifuge section 706. The fuel vaporizing section 702 is illustrated as having two fuel injectors 708 for inputting fuel into the centrifugal vortex system 700. The fuel injectors 708 are coupled to a fuel rail 710 having a passageway 712 passing therethrough from an input end 714 to an output end 716. The input end 714 of the passageway 712 is coupled to a conventional fuel pump (not shown) and the output end 716 is coupled to a conventional fuel regulator (not shown) which is, in turn, coupled to a return line back to the fuel tank (not shown).

The fuel injectors 708 are mounted within the centrifugal vortex system 700 by injector plates 720. Fuel is sprayed from fuel injector output ports 722 into two vortex configurations 611 each vortex configuration 611 being identical to the vortex configuration 611 illustrated in FIG. 19. The two vortex configurations 611 are positioned adjacent to the fuel injector plates 720 and are in fluid communication with the output ports 722 of the fuel injectors 708 to allow aerosol fuel to be sprayed directly into the two vortex configurations 611 from the output ports 722.

The two vortex configurations 611 are mounted within an air box 724. The air box 724 is shown as comprising a side wall 726, a side wall 728, a base plate 730, and a top plate 732. An air chamber 734 is formed within the air box 724 as a conduit between an ambient air conduit 736 and the apertures 636 (FIG. 19) formed in the vortex configurations 611.

The ambient air conduit 736 is illustrated as comprising a rubber hose 740. The ambient air conduit 736 interconnects an ambient air slot 742 with the chamber 734 for providing ambient air to the vortex configurations 611. As shown, the hose 740 is coupled to the slot 742 via a threaded connector 741.

The vortex configurations 611 are secured within the air box 724 by a bracket 744 interposed between the output flange 640 (FIG. 19) of each vortex configuration 611 and the inside surface 748 of the top plate 732. The output port 648 (FIG. 19) of each vortex configuration 611 discharges fluid into an intermediate mixing chamber 750 formed in the main air section housing 752. The intermediate mixing chamber 750 generally causes a spinning column of fluid exiting the output port 648 (FIG. 19) to enfold and to mix turbulently prior to entering the venturi 756 through a series of elongated apertures 770. The described activity of the fluid in the intermediate mixing chamber 750 further breaks down into smaller particles and further vaporizes and homogenizes the liquid particles in the vortical flow.

The main air section 704 further comprises an ambient air intake port 760 to permit a flow of air F to enter the main air section 704 through the port 760. A conventional throttle plate 762 is pivotally secured within the venturi 756. The throttle plate 762 is secured to a rotatable central shaft 764, which is oriented transverse to the direction of air flow F through the venturi 756. Rotation of the shaft 764 will adjust an inclination angle of the throttle plate 762 within the venturi 756, thereby changing the volume of air and thus the air/fuel mixture admitted to the engine.

As mentioned above, an air/fuel mixture passes from the vortex configurations 611 into the intermediate mixing chamber 750. The air/fuel mixture then passes through the intermediate mixing chamber output 758 and into the venturi 756 through a series of elongated apertures 770. Thus, within the venturi 756, ambient air passing across the throttle plate 762 is mixed with an air/fuel mixture passing through the apertures 770.

The centrifuge section 706 is rigidly affixed to the main air section housing 752 by fasteners such as screws 772 and 774. The centrifuge section 706 is shown as comprising a transition housing 776 having an inside surface 778 and an outside surface 780. The inside surface 778 defines a transition passageway 782 for passing fluid from the venturi 756 into a centrifuge chamber 784. As shown, the transition passageway 782 is oriented substantially tangentially to the centrifugal vortex system chamber 784 for inputting fluid into the centrifuge chamber 784 in a substantially tangential manner. By orienting the transition passageway 782 substantially tangentially to the centrifuge chamber 784, the air resistance through the system is reduced and the centrifugal flow of fluid through the centrifuge chamber 784 is enhanced.

An extension arm 788 is positioned adjacent to the passageway 782 and extends into the centrifuge chamber 784 to prevent fluid from re-entering the passageway 782 after being discharged into the chamber 784. The extension arm 788 is shown as comprising a wall 790 having a front surface 792 and a rear surface 794. As shown, the extension arm 788 is mounted on and extends from the transition housing 776. The front surface 792 and the rear surface 794 are intersected at one end by transverse surface 796. Thus, as fluid flow from the venturi 756 passes through the intermediate chamber 782 into the centrifuge chamber 784, the return of fluid from the centrifuge chamber 784 back into the intermediate chamber 782 is substantially prevented, if not eliminated, by the presence of the extension arm 788. As illustrated, the front surface 792 of the extension arm 788 is curved to enhance the centrifugal flow of fluid in the centrifuge chamber 784 while, at the same time, substantially preventing fluid from re-entering the passageway 782.

The centrifuge section 706 further comprises a vertically directed cylindrical wall 798 having an inside surface 800 and an exterior surface 802. A centrifuge bottom surface 804 is positioned in a substantially perpendicular orientation with the inside surface 800 of the centrifuge housing and has an output conduit 806 defined by a cylindrical surface 808 for discharging fluid from the centrifuge chamber 784 to an internal combustion engine intake manifold (not shown).

Mounting extensions 810 are illustrated as being mounted on the exterior surface 802 of the centrifuge housing 798 for securing the centrifuge housing to an interface plate or other mounting apparatus in connection with an internal combustion engine intake manifold. Each mounting extension 810 further comprises an aperture 812 for passing a fastener through the mounting extension.

Figure 22:
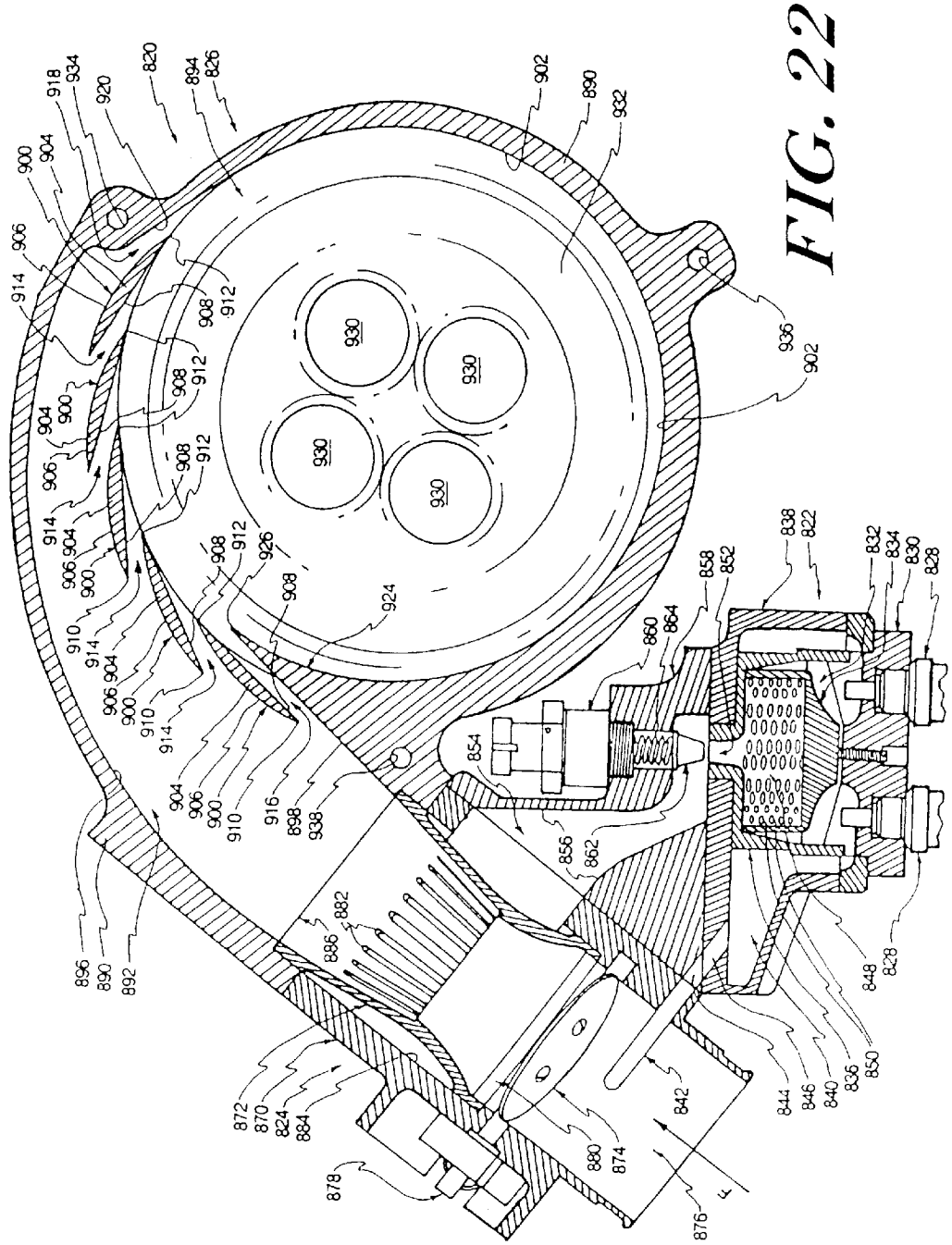
FIG. 22 is a top sectional view of yet another alternative embodiment of a centrifugal vortex system according to the present invention.

FIG. 22 illustrates a yet additional alternate embodiment of a centrifugal vortex system according to the present invention. This embodiment shows a centrifugal vortex system 820. The centrifugal vortex system 820 is illustrated as comprising three sections: fuel vaporizing section 822, a main air section 824, and a centrifuge section 826. The fuel vaporizing section 822 is illustrated as having two fuel injectors 828 mounted within an injector plate 830 for spraying fuel into a preliminary mixing chamber 832. The fuel injectors 828, fuel injector plate 830, and preliminary mixing chamber 832 are configured and operate substantially the same as the fuel injectors 38, the injector plate 42, and the preliminary mixing chamber 43 illustrated in FIG. 1 and described above.

The fuel vaporizing section 822 further comprises a vortex chamber housing 834 and a jacket 836 positioned within a housing 838. The vortex chamber housing 834, the jacket 836, and the housing 838 are configured and function in substantially the same manner as the vortex chamber housing 54, the jacket 60, and the housing 74 described above and illustrated in FIGS. 1 and 3. The housing 838 further comprises an ambient air receiving chamber 840 for receiving ambient air from the ambient air slot 842 via conduit 844 and aperture 846.

Ambient air and fuel are introduced into the vortex chamber 848 from the preliminary mixing chamber 832 via apertures 850. The air/fuel mixture is output through an output port 852 into an intermediate channel 854 defined by an inner wall surface 856 of an intermediate housing 858.

A linear actuator, such as a stepper motor 860 identical to the stepper motor 676 illustrated in FIG. 20 and described above is threadedly engaged within the intermediate housing 858 and is illustrated as being substantially aligned and coaxial with the output port 852. The stepper motor 860 further comprises a conical plug 862. The stepper motor 860 acts as a linear actuator to move the conical plug 862 via a shaft 864 relative to the output port 852 for selectively providing flow resistance at the output port 852.

When the shaft 864 is in a fully extended position (not shown), the conical plug 862 contacts and substantially seals the output port 852 to substantially prevent fluid passage through the output port 852. In the fully retracted position illustrated in FIG. 22, the conical plug 862 provides little, if any, flow resistance. Thus, the closer the conical plug 862 is positioned to the output port 852, the more fluid resistance will be imparted by the conical plug 862. As such, the flow resistance through the output port 852 can be varied by causing the stepper motor 860 to selectively position the conical plug 862 relative to the output port 852.

After fluid passes from the output port 852 past the conical plug 862 and into the intermediate channel 854, the fluid next enters the main air section 824. As shown, the main air section 824 comprises a main air housing 870, a venturi 872, and a conventional throttle plate 874. The main air section 824 is configured and operates in substantially the same manner as the main air section 34 described above and illustrated in FIG. 1. The throttle plate 874 is pivotally secured to a rotatable central shaft 878, which is oriented transverse to the direction of air flow F through the chamber 876. Rotation of the shaft 878 will adjust an inclination angle of the throttle plate 874 within chamber 876, thereby changing the volume of air and thus the air/fuel mixture admitted to the engine.

Ambient air passes past the throttle plate 874 into the venturi 872 through a venturi input 880. An air/fuel mixture enters the venturi 872 through a series of elongated apertures 882 from the channel 854. The venturi input 882 is secured within an interior surface 884 of the housing 870. The venturi output 886 is attached to the centrifuge housing 890.

The centrifuge housing 890 comprises an entry chamber 892 and a centrifuge chamber 894. The entry chamber 892 is defined by a curved inside surface 896 and flat inside surface 898. A series of baffles 900 are oriented tangentially relative to the centrifuge chamber interior surface 902. Each baffle 900 comprises a vertically directed wall 904 having a curved surface 906 and a flat surface 908. The curved surface 906 and the flat surface 908 of each baffle intersect at a leading edge 910 and at a trailing edge 912. The baffles 900 form a plurality of tangential passageways 914 for inputting fluid tangentially from the entry chamber 892 into the centrifuge chamber 894.

A tangential passageway 916 is also formed between the flat edge 898 of the entry chamber 892 and the flat edge 908 of the baffle 900 adjacent to the flat edge 898 for admitting fluid tangentially into the centrifuge chamber 894. Likewise, a tangential passageway 918 is formed between the curved surface 906 and a flat surface 920 formed on the chamber housing 890 for admitting fluid tangentially into the centrifuge chamber 894.

An extension arm or diverter 924 is illustrated as being integrally formed with the chamber housing 890 and terminates at edge 926. The extension arm 924 eliminates or substantially prevents fluid from the chamber 894 from exiting the chamber through the entry chamber 892. Indeed, the extension arm 924 directs fluid passing adjacent to the entry chamber 892 away from the passageway 916. While configured slightly differently, the extension arm 924 and the extension 788 illustrated in FIG. 21 serve essentially the same purpose, that is to prevent fluid from escaping the centrifuge chamber and passing back into the venturi.

The centrifuge section 826 further comprises output passageways configured identical to output passageways illustrated in FIG. 1 and described above. The centrifuge chamber bottom surface 932 also comprises a contoured bottom insert identical to the contoured bottom insert 166 illustrated in FIGS. 1 and 2.

Mounting apertures 934, 936, and 938 are also formed in the chamber housing 89 to permit the chamber housing to be rigidly secured via an interface plate (not shown) to an intake manifold of an internal combustion engine.

FIG. 23 shows yet another alternate embodiment of a vortex chamber housing according to the present invention. This embodiment shows a vortex chamber housing 940 generally comprising a bottom wall 942 and a perpendicularly extending cylindrical wall 944. The cylindrical wall 944 comprises an inside surface 946, a top edge 947, and an outside surface 948. A vortex chamber 952 is defined by the inside surface 946 and the bottom wall 942. The vortex chamber housing 940 may be used in a manner similar to that of the vortex chamber housing 54 illustrated in FIG. 1 and described above.

A series of elongated tangential slots 950 are formed through the wall 944 from the outside surface 948 to the inside surface 946 for delivering a fluid tangentially into the vortex chamber 952 relative to the vortical flow of fluid inside the chamber. Each slot 950 is shown as extending without interruption from the top edge 947 of the wall 944 to the chamber housing bottom wall 942. The slots 950 are oriented tangentially to the inside cylindrical surface 946 of the annular wall 944 to permit fluid to be introduced tangentially to the vortical flow into the vortex chamber 952 of the vortex chamber housing 940.

Introducing fluid tangentially into the chamber 952 through the elongated slots 950 creates a continuous sheet of moving fluid passing rapidly across the vortex chamber interior surface 946 adjacent the respective slots 950. This substantially prevents any non-vaporized particles within the flow of fluid from congregating on the interior surface 946. As droplets of non-vaporized fluid particles approach or contact the inside surface 946, such non-vaporized particles are blown away from the inside surface by new fluid-flow particles entering the vortex chamber 952 through the slots 950. Any number of slots 950 may be employed to achieve the desired results. Additionally, different widths of the slots 950 may be used. The slots 950 may be formed in the annular wall 944 with a laser, a circular saw, or by any other suitable method. As one example, slots 950 may have a width of approximately 0.01 inches.

FIGS. 24 and 25 illustrate another alternate embodiment of a venturi according to the present invention. This embodiment shows a venturi 954 comprising a housing 956 and a series of tangential apertures 958 formed in the housing 956. The tangential apertures extend from a housing exterior surface 955 to a housing interior surface 957. The apertures 958 are formed tangentially in the housing 956 to permit fluid, such as an air/fuel mixture, to be inserted into the venturi interior 960 tangentially through the apertures 958 to enhance the turbulence of the flow through the venturi 954.

As shown, the tangential apertures 958 are formed within a narrow throat portion 959 of the venturi 954. In the narrow throat portion 959, the speed of the fluid F passing through the venturi 954 is at a maximum. By introducing a second fluid tangentially into the venturi interior 960 through the tangential apertures 958 in the narrow throat portion 959, the turbulence and mixing of the two fluids is enhanced. Delivery of the second fluid tangentially into the venturi interior 960 through the tangential apertures 958 causes the flow through the venturi interior 960 to spin, thus increasing the turbulence of the flow. The enhanced turbulence of the flow through the venturi 954 further enhances the vaporization and homogenization of the fluid passing through the venturi 954. Accordingly, as the fluid flow F passes through the venturi from the venturi entrance 962 to the venturi 964, the flow is intersected by a tangential flow of a second fluid, such as an air/fuel mixture, entering the venturi interior 960 through the tangential apertures 958 to create a turbulent, and substantially helical, flow through the venturi 954.

Figure 27:
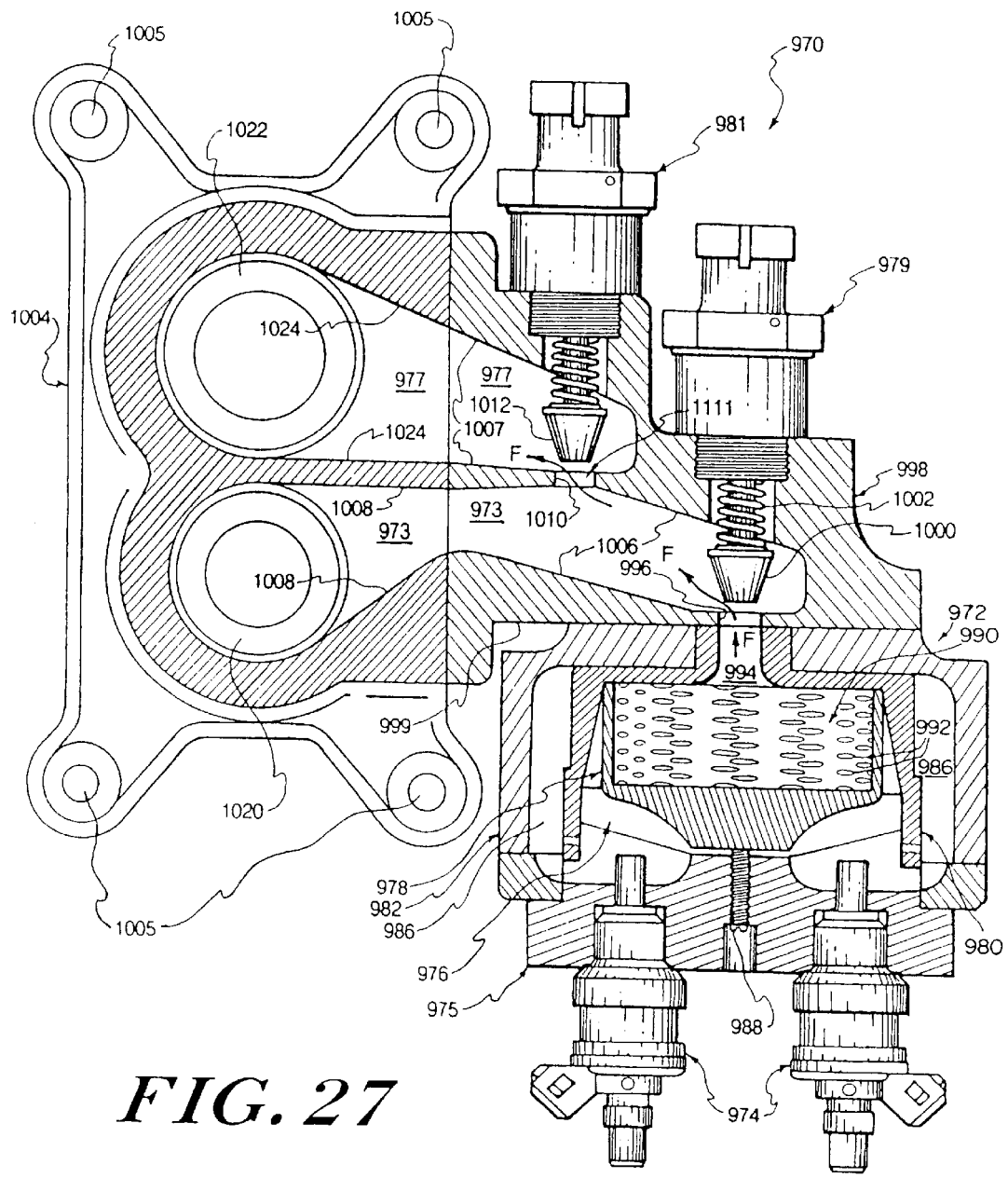
FIG. 27 is a partial sectional side elevation view, taken along the line 27—27 of FIG. 26, of the centrifugal vortex system of the present invention.
Figure 28:
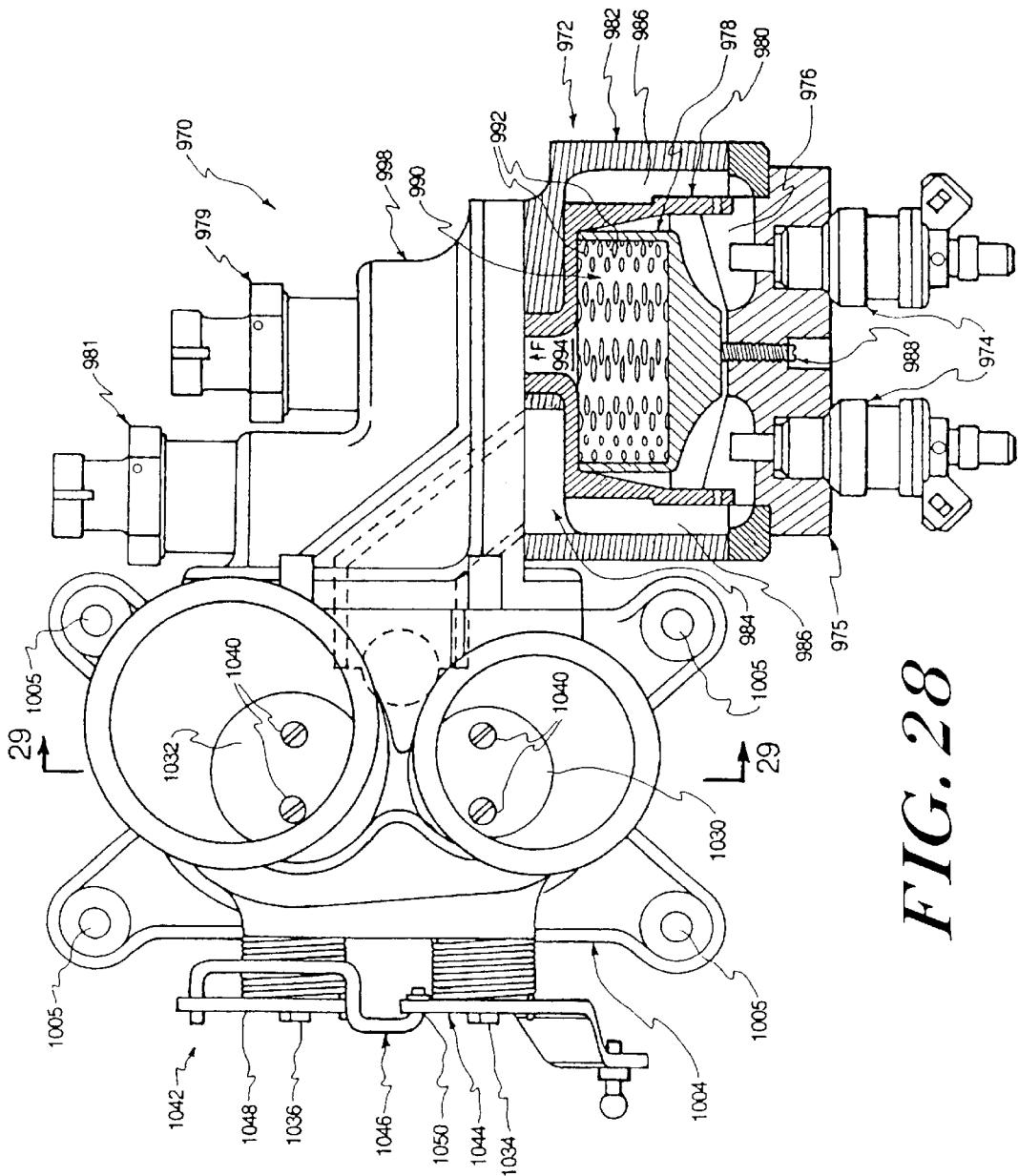
FIG. 28 is a partial sectional side elevation view of the centrifugal vortex system shown in FIG. 26.

FIGS. 26–30 illustrate a yet additional alternate embodiment of a centrifugal vortex system according to the present invention. FIG. 27 shows a centrifugal vortex system 970 which generally comprises a vortex chamber assembly 972, a primary throat 973, a secondary throat 977, a primary stepper motor 979, and a secondary stepper motor 981. As shown in FIGS. 27 and 28, the vortex chamber assembly 972 is configured in a manner similar to the vortex chamber assembly 822 illustrated in FIG. 22. Specifically, the vortex chamber assembly 972 is illustrated as having two fuel injectors 974 mounted within an injector plate 975 for spraying fuel into a preliminary mixing chamber 976. The fuel injectors 974, the fuel injector plate 975, and the preliminary mixing chamber 976 are configured and operate in substantially the same manner as the fuel injectors 828, the fuel injector plate 830, and the preliminary mixing chamber 832 illustrated in FIG. 22 and described above.

The vortex chamber assembly 972 further comprises a vortex chamber housing 978 and a jacket 980 positioned about the vortex chamber housing 978 within a fuel vaporizing housing 982. The vortex chamber housing 978, the jacket 980, and the fuel housing 982 are configured and function in substantially the same manner as the vortex chamber housing 834, the jacket 836, and the fuel vaporizing housing 838 described above and illustrated in FIG. 22. The housing 982 further comprises an ambient air receiving port 984 (FIG. 28) for receiving ambient air into the preliminary mixing chamber 976 through an annular conduit 986. A set screw 988 is threadedly engaged with the fuel injector plate 975 and secures the vortex chamber housing 978 within the vortex chamber assembly 972.

As shown in FIGS. 27 and 28, ambient air and fuel are introduced into the vortex chamber 990 via apertures 992. Ambient air is introduced into the preliminary mixing chamber 976 through the conduit 986. Fuel is delivered into the preliminary mixing chamber 976 by injectors 974. The air and fuel are allowed to mix in the preliminary mixing chamber prior to entering the vortex chamber 990. The air/fuel mixture is then drawn into the vortex chamber 990 through an array of tangential apertures 992 to create a vortical flow of fluid in the vortex chamber 990. The vortical flow serves to break down moisture particles. After spinning vertically in the chamber 990, the air/fuel mixture is output through an output port 994 into the primary throat 973 through an aperture 996 formed in an intermediate housing 998. The intermediate housing 998 is secured to the housing 982 along a contact surface 999 such that the output port 994 and the aperture 996 are substantially aligned.

With continued reference to FIG. 27, a primary linear actuator, such as a stepper motor 979, is threadedly engaged with the intermediate housing 998 and is shown as being substantially aligned and coaxial with the aperture 996 and the output port 994. The stepper motor is identical to the stepper motor 676 illustrated in FIG. 20 and described above. A conical plug 1000 is coupled to the stepper motor 978 via a spring-biased shaft 1002. The stepper motor 979 acts as a linear actuator to move the conical plug 1000, via a shaft 1002, relative to the aperture 996 and the output port 994 to selectively restrict the flow through the output port 994.

When the shaft 1002 is in a fully extended position (not shown), the conical plug 1000 engages, and substantially seals, the aperture 996 to substantially prevent fluid passage through the output port 994 into the primary throat 973. In a fully retracted position (not shown), the conical plug 1000 provides little, if any, flow resistance. Thus, the closer the conical plug 1000 is positioned to the output port 994 and the aperture 996, the more flow resistance is imparted by the conical plug 1000. As such, the flow resistance through the output port 994 and the aperture 996 can be controlled by causing the stepper motor 979 to selectively position the conical plug 1000 relative to the aperture 996 and the output port 994.

After fluid passes from the output port 994, through the aperture 996, and past the conical plug 1000, the fluid enters the primary throat 973. As shown, the throat 973 comprises a passageway formed in the intermediate housing 998 and in the output housing 1004. Within the intermediate housing 998, the primary throat 973 is defined by an interior surface 1006. Similarly, within the output housing 1004, the primary throat 973 is defined by an interior surface 1008. The output housing 1004 further comprises a plurality of mounting apertures 1005 for securing the centrifugal vortex system 970 to a conventional engine (not shown).

An aperture 1010 is formed in the intermediate housing 999 from the interior surface 1006 of the primary throat 973 to an interior surface 1007 of the secondary throat 977. As shown, the aperture 1010 defines a passageway 1111 which interconnects the primary throat 973 with the secondary throat 977. Thus, when the passageway 1111 is not blocked, fluid may flow from the primary throat 973 into the secondary throat 977 through the passageway 1111.

A secondary linear actuator, such as stepper motor 981, is also threadedly engaged with the intermediate housing 998 and is illustrated as being substantially aligned and coaxial with the aperture 1010 and is coupled to a conical plug 1012 via a shaft 1014. The stepper motor 981 acts as a linear actuator to move the conical plug 1012, via the shaft 1014, relative to the aperture 1010 for selectively providing flow resistance or substantially sealing the aperture 1010.

When the shaft 1014 is in a fully extended position (not shown), the conical plug 1012 contacts and substantially seals the aperture 1010 to substantially prevent fluid passage from the primary throat 973 into the secondary throat 977 through the passageway 1111. In a fully retracted position (not shown), the conical plug 1012 imparts little, if any, flow resistance to a flow of fluid passing from the primary throat 973 into the secondary throat 977 through the passageway 1111. Thus, the closer the conical plug 1012 is positioned to the aperture 1010, the more flow resistance is imparted by the conical plug 1012. As such, the flow resistance, and thus the flow, through the passageway 1111 can be controlled by actuation of the stepper motor 981 to selectively position the conical plug 1012 relative to the aperture 1010.

Figure 29:
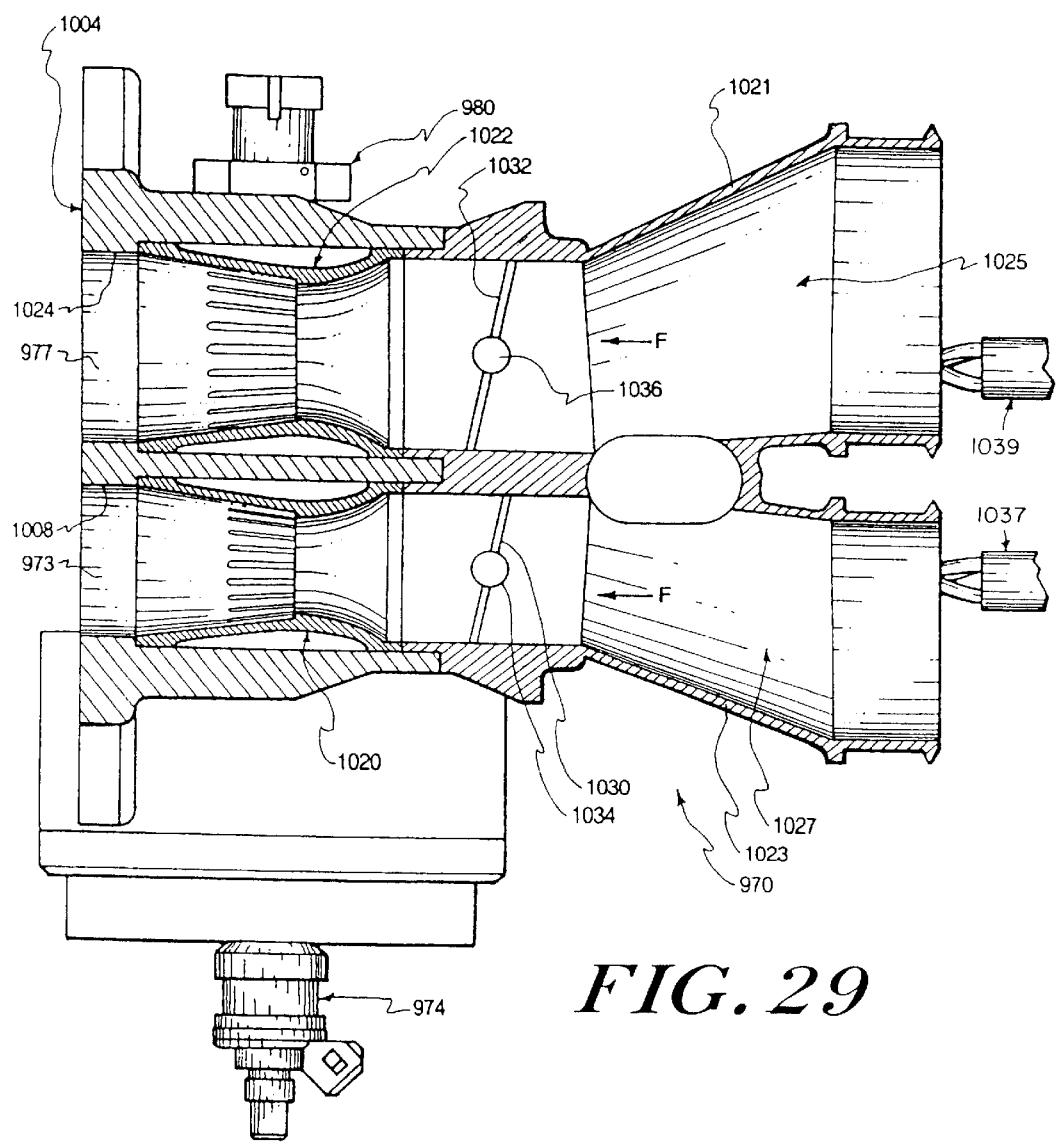
FIG. 29 is a partial sectional view, taken along the line 29—29 of FIG. 28, of the centrifugal vortex system according to the present invention.

As shown in FIGS. 27 and 29, a primary venturi 1020 is positioned within an interior surface 1008 of the primary throat 973. Similarly, a secondary venturi 1022 is positioned within an interior surface 1024 of the secondary throat 977. The venturis 1020 and 1022 are configured and operate in substantially the same manner as the venturi 872 illustrated in FIG. 22. It should be noted that, however, the venturi 954 illustrated in FIGS. 24 and 25 and described above may also be effectively employed in this embodiment.

FIG. 29 illustrates that ambient air enters the system 970 through ambient air ducts 1021 and 1023. The air ducts 1021 and 1023 respectively define duct interior passageways 1025 and 1027. To control the amount of ambient air entering the venturis 1020 and 1022 through the respective venturi openings 1026 and 1028, throttle plates 1030 and 1032 are provided. The throttle plates 1030 and 1032 are pivotally secured to rotatable shafts 1034 and 1036, respectively. The rotatable shafts 1034 and 1036 are oriented transverse to the direction of airflow through the venturis 1020 and 1022. The rotation of the shafts 1034 and 1036 adjusts an inclination angle of the throttle plates 1030 and 1032, respectively, thereby changing the volume of air and thus the air/fuel mixture admitted to the engine. As shown in FIG. 28, the throttle plates 1030 and 1032 are secured to the shafts 1034 and 1036 respectively by fasteners, such as screws 1040 (FIG. 28).

As illustrated in FIGS. 27 and 29, the secondary throat 977 is larger, and thus capable of accommodating more flow, than the primary throat 973. Similarly, the secondary venturi 1022 is larger, and thus capable of accommodating more flow than the primary venturi 1020. As discussed in more detail below, the primary throat 973 and the primary venturi 1020 are used exclusively at lower engine RPM's to enable a high resolution engine response. At higher engine RPM's, both the primary and secondary throats 973 and 977 are utilized to enable the system to attain a high volumetric efficiency.

Figure 30:
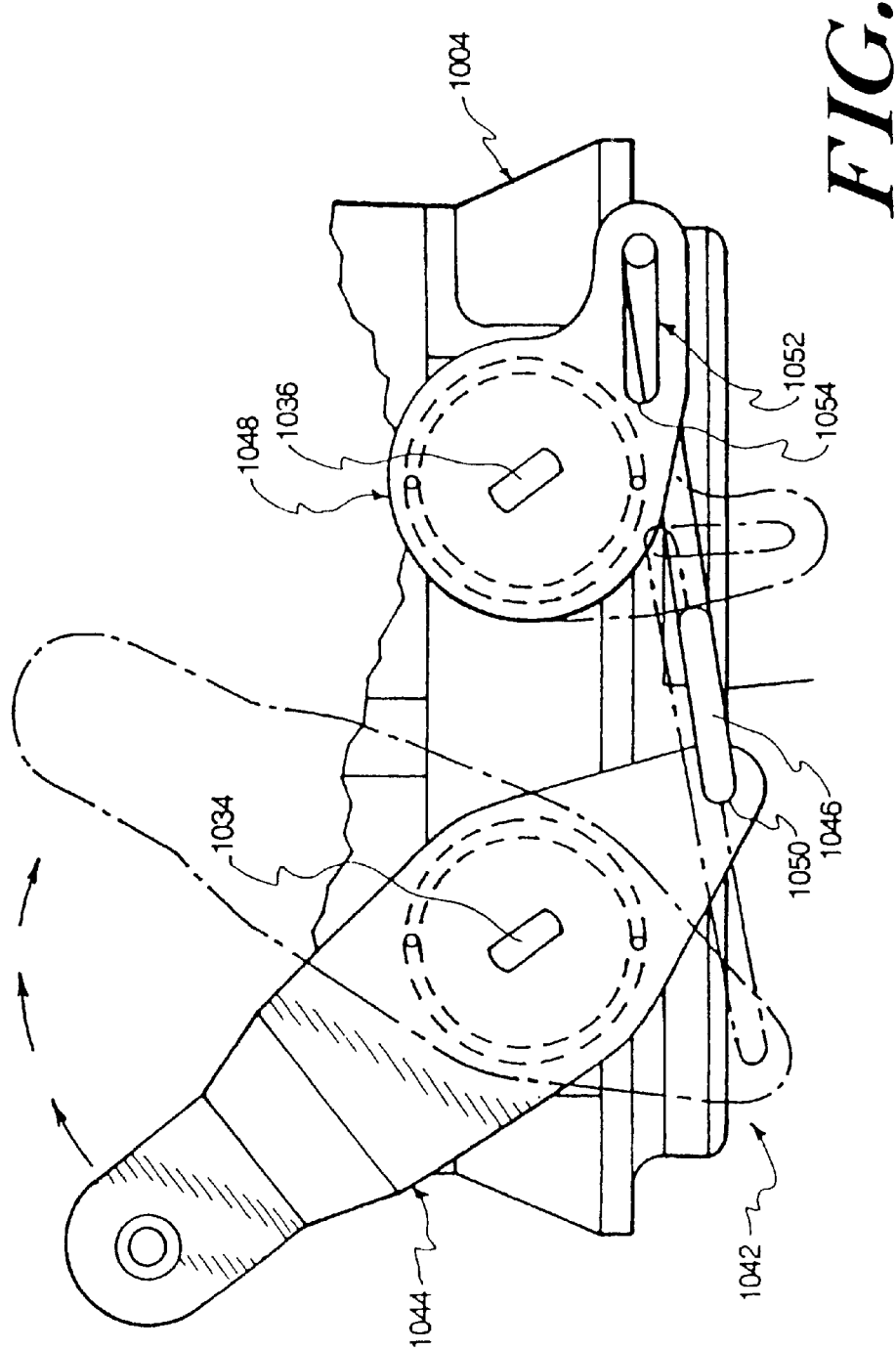
FIG. 30 is an enlarged view of the linkage assembly illustrated in FIG. 29.

With reference to FIGS. 26, 28, and 30, the position of the throttle plates 1030 and 1032 is controlled by a linkage assembly 1042. The linkage assembly 1042 is shown as generally comprising a primary lever arm 1044, a connecting link 1046, and a secondary lever arm 1048. The secondary arm 1048 is biased toward the closed position shown in FIGS. 26 and 30. The primary arm 1044 is rigidly secured to the primary shaft 1034 such that as the primary arm 1044 pivots relative to the output housing 1004, the primary shaft 1034 also pivots, thus causing the primary throttle plate 1030 to pivot. Likewise, the secondary arm 1048 is rigidly secured to the secondary shaft 1036 so that as the secondary arm 1048 rotates relative to the output housing 1004, the secondary shaft 1036, and thus the secondary throttle plate 1032, are caused to pivot. The link 1046 is shown as being pivotally secured to the primary arm 1044 through an aperture 1050. The opposite end of the link is slidably positioned within an elongated slot 1052 formed in the secondary arm 1048.

With reference to FIGS. 26 and 30, the linkage assembly 1042 is illustrated as being in a closed position with both the primary and secondary throttle plates 1030 and 1032 being substantially closed. As the primary arm 1044 rotates about the primary shaft 1034 in a clockwise direction, the primary throttle plate 1030 (FIG. 28) opens and admits air into the primary venturi 1020 (FIG. 29). Additionally, as the primary arm 1044 rotates clockwise, the link 1046 slides along the slot 1052 formed in the secondary arm 1048. As the primary arm 1044 continues to rotate clockwise, further opening the primary throttle plate 1030, the link 1046 advances through the slot 1052 until it contacts the slot end 1054. Once the link 1046 has contacted the slot end 1054, any additional clockwise rotation of the primary arm 1044 causes the secondary arm 1048 to rotate, thus causing the secondary throttle plate 1032 to pivot and open the secondary throat. The link 1046 contacts the slot end 1054 when the primary throttle plate 1030 is opened a predetermined amount. In one embodiment, this predetermined amount is approximately 40% open.

By continuing to rotate the primary arm 1044 clockwise after the link 1046 is in contact with the slot end 1054, the link 1046 causes the secondary arm 1048 to rotate clockwise, thus opening the secondary throttle plate 1032. That is, once primary throttle plate is opened 40% toward being fully opened, the link 1046 engages the slit end 1054 and the secondary throttle plate 1032 starts to open. In the filly open position illustrated in phantom in FIG. 30, the primary and secondary arms 1044 and 1048 are oriented such that both throttle plates 1030 and 1032 are fully open. As discussed in more detail below, rotating the primary arm 1044 counterclockwise causes the primary and secondary throttle plates 1030 and 1032 to close.

With reference to FIG. 27, it is advantageous for the secondary linear actuator 981 to remove the conical plug 1012 from within the aperture 1010 as the secondary throttle plate 1032 begins to open. In this manner, the primary throat 973 is the exclusive flow path for the air/fuel mixture at low engine RPM's when the primary throttle plate 1030 is opened less than a predetermined amount, such as 40%. As the primary throttle plate continues to open past the predetermined amount, the plug 1012 is removed from the aperture 1010 and the secondary throttle plate 1032 is opened to permit the air/fuel mixture to pass through both the primary and secondary throats 973 and 977 to enhance the volumetric efficiency of the system at higher engine RPM's. The positions of the throttle plates 1030 and 1032 can be continuously monitored by throttle plate sensors coupled to the shafts 1034 and 1036 through sensor connectors 1037 and 1039 (FIG. 26). Accordingly, in this manner, a relatively high resolution response can be attained at low engine RPM's by using the smaller primary throat 973 exclusively. Then, at higher engine RPM's, when volumetric efficiency is desired, the secondary throat 977 may be used in addition to the primary throat 973.

Figure 31:
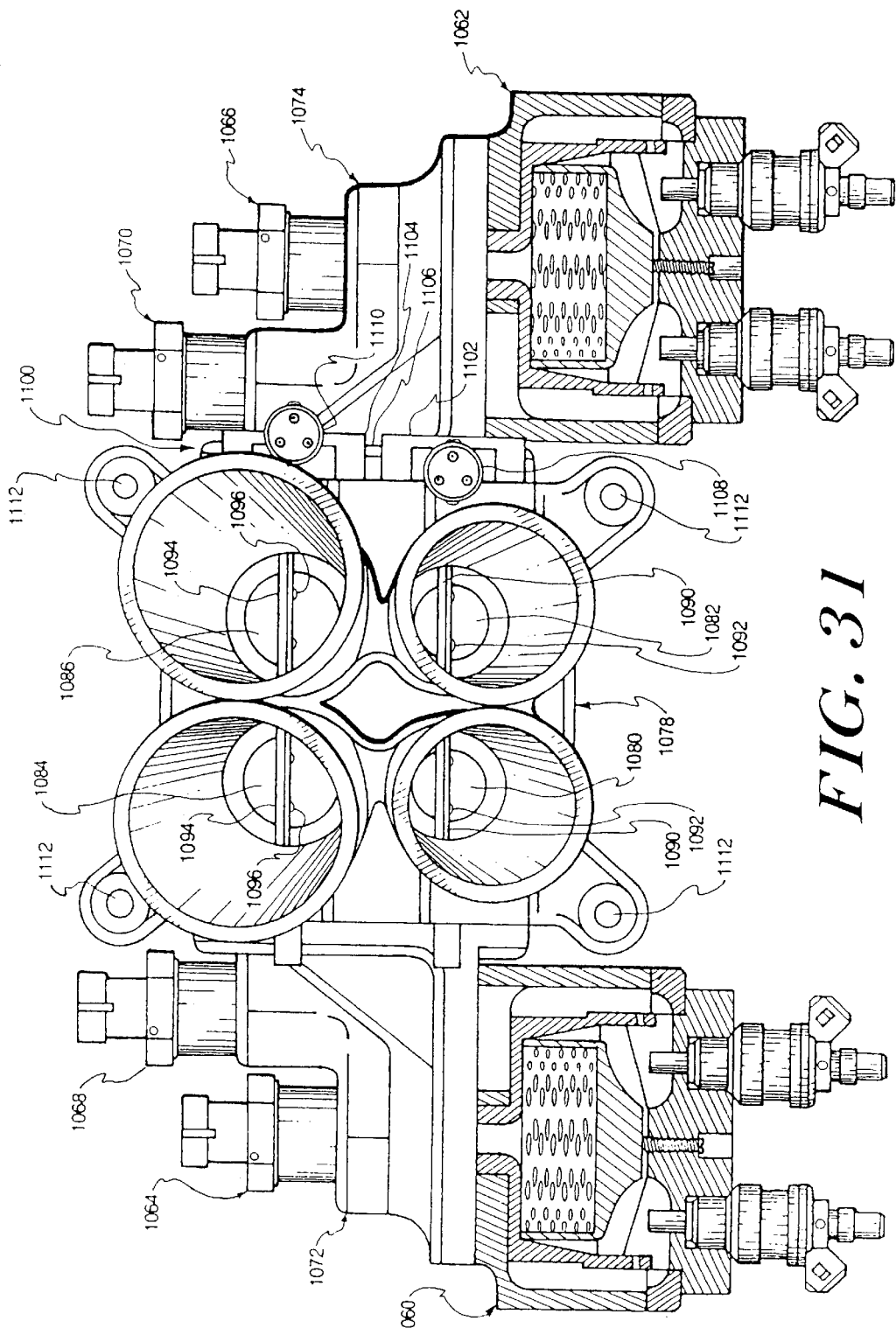
FIG. 31 is a sectional side elevation view of yet another alternate embodiment of a centrifugal vortex system according to the present invention.

FIG. 31 shows another alternative embodiment of the present invention. The embodiment of FIG. 31 generally demonstrates that the structures and methods illustrated in FIGS. 26–30, described above, can also be used in connection with a four-barrel carburetor system. One side of the four-barrel system is essentially a mirror image of the other. Specifically, FIG. 31 illustrates two vortex chamber assemblies 1060 and 1062. Each vortex chamber assembly 1060 and 1062 is configured identically to and operates in the same manner as the vortex chamber assembly 972 illustrated in FIGS. 27 and 28 and described above. Likewise, the embodiment of FIG. 31 illustrates two primary linear actuators 1064 and 1066. The primary linear actuators 1064 and 1066 are configured and operate in the same manner as the primary linear actuator 979 illustrated in FIG. 27 and described above. Further, FIG. 31 illustrates two secondary linear actuators 1068 and 1070 which are configured and operate the same as the secondary linear actuator 981 illustrated in FIG. 27 and described above.

The linear actuators 1064 and 1068 are mounted within a first intermediate housing 1072. The intermediate housing 1072 is configured and operates in a manner identical to that of the intermediate housing 998 illustrated in FIG. 27 and described above. Likewise, the linear actuators 1066 and 1070 are also mounted within an intermediate housing 1074 which is configured and operates in a manner identical to the intermediate housing 998 illustrated in FIG. 27 and described above.

An output housing 1078 is positioned between the intermediate housings 1072 and 1074. The output housing 1078 is similar to the output housing 1004 illustrated in FIGS. 26–29 and described above. The primary difference between the output housing 1078 and the output housing 1004 is that the output housing 1078 is configured with two adjacent primary throats and two adjacent secondary throats for accommodating flow through two primary throttle plates 1080 and 1082 and two secondary throttle plates 1084 and 1086 respectively.

The primary throttle plates 1080 and 1082 are configured and operate the same as the primary throttle plate 1030 illustrated in FIG. 29 and described above. Likewise, the secondary throttle plates 1084 and 1086 are configured and operate in the same manner as the secondary throttle plate 1032 illustrated in FIG. 29 and described above. The primary throttle plates 1080 and 1082 are both rigidly attached to a single primary shaft 1090 by fasteners 1092. Likewise, the secondary throttle plate 1084 and 1086 are secured to a secondary shaft 1094 by fasteners 1096.

The positions of the primary throttle plates 1080 and 1082 as well as the positions of the secondary throttle plates 1084 and 1086 are controlled by a linkage system 1100. The linkage system 1100 comprises a primary arm 1102, a secondary arm 1104, and a link 1106. The primary arm 1102, the secondary arm 1104, and the link 1106 are configured and operate in substantially the same manner as the primary arm 1044, the secondary arm 1048, and the link 1046 of the linkage system 1042 illustrated in FIGS. 26 and 30 and described above. Further, to monitor the positions of the throttle plates, throttle plate sensors 1108 and 1110 are coupled with the shafts 1090 and 1094 respectively. The output housing 1078 may be readily secured to a conventional engine (not shown) by conventional mounting apertures 1112.

Figure 32:
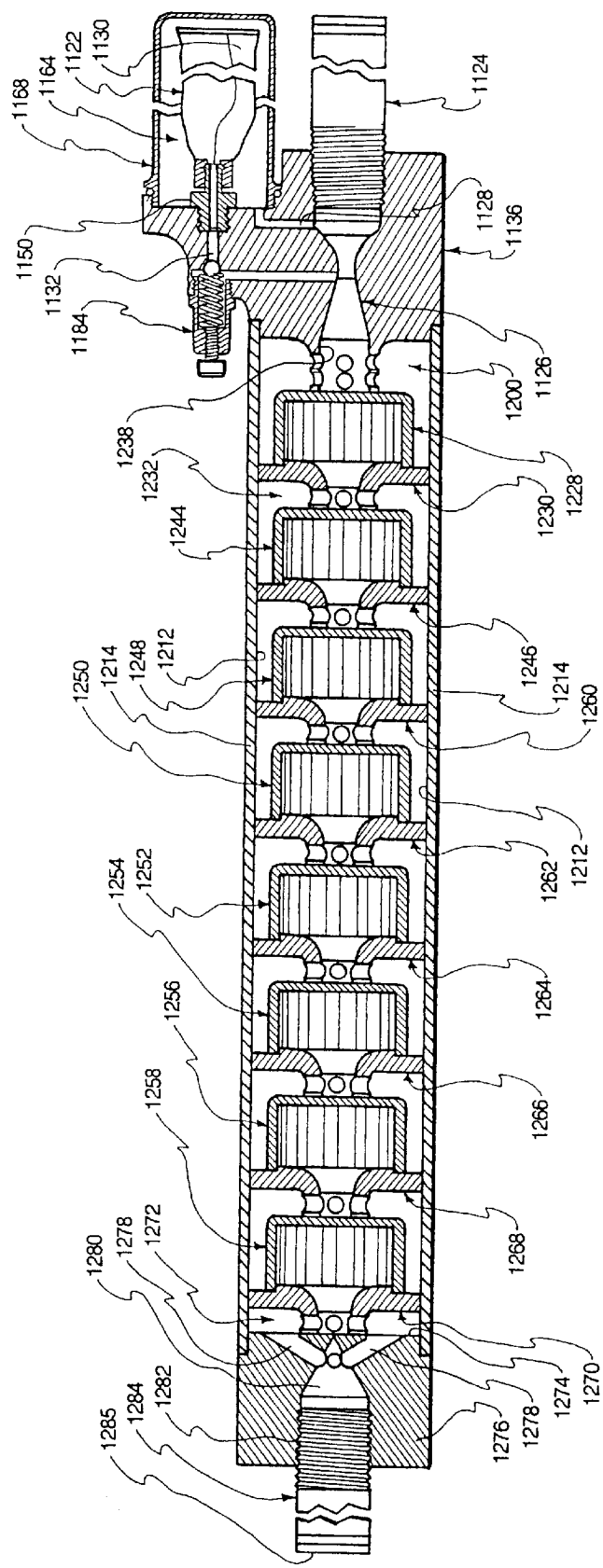
FIG. 32 is a sectional side elevation view of still another alternate embodiment of a centrifugal vortex system for vaporizing a fluid according to the present invention.
Figure 33:
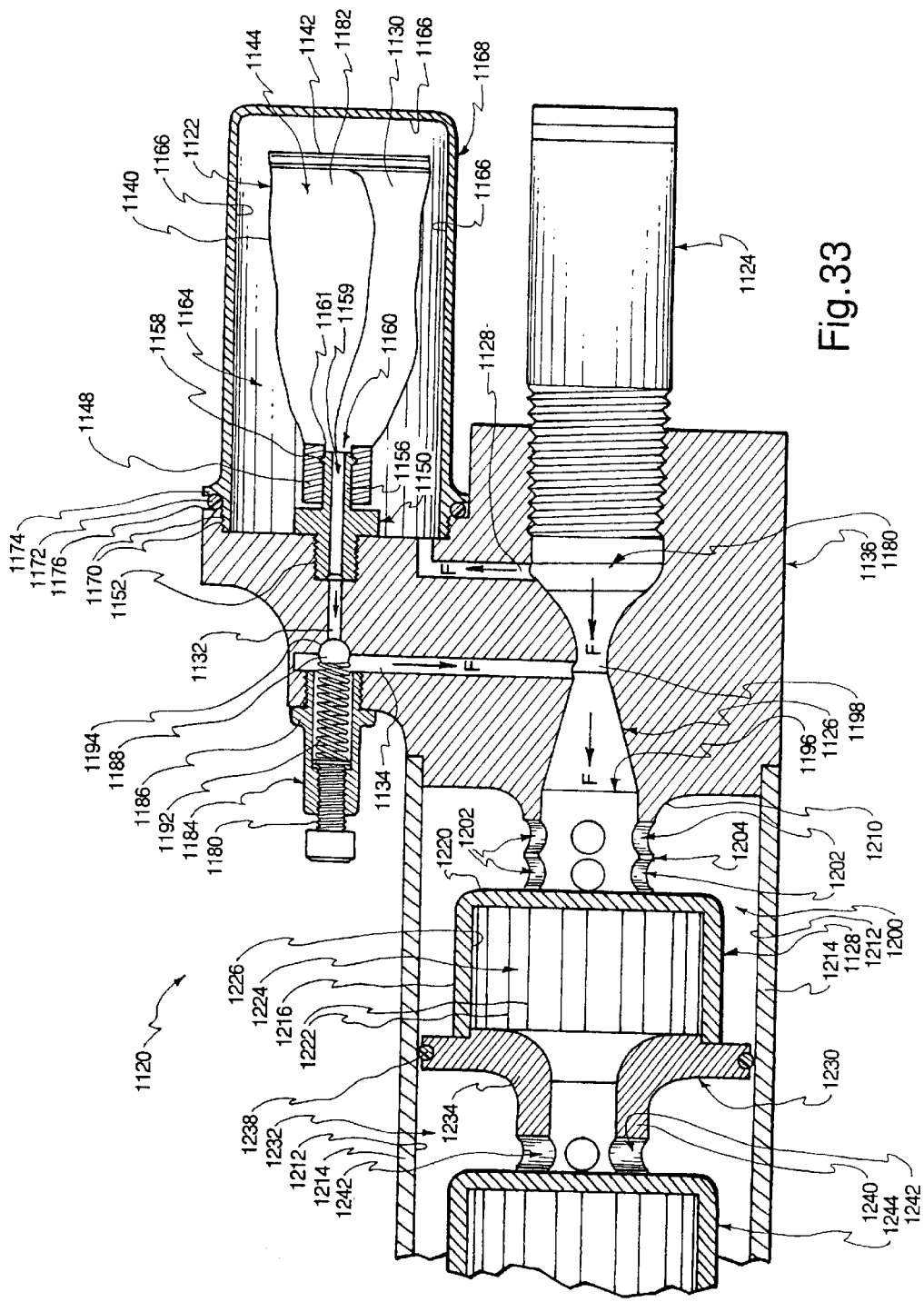
FIG. 33 is an enlarged sectional view of a portion of the embodiment illustrated in FIG. 32.

FIGS. 32 and 33 illustrate a yet additional alternative embodiment of the present invention, specifically in relation to uses in the field of inhaler-type medications. This embodiment shows a fluid vaporization system 1120 generally comprising a compressible container 1122, a supply of pressurized gas 1124, a venturi 1126, a plurality of vortex chamber housings 1128, 1244, 1248, 1250, 1252, 1254, 1256, 1258, and a system output 1128. Generally, by introducing pressurized gas into the system 1120, a fluid flow 1130 is forced out of the compressible container 1122 and is caused to flow through conduits 1132 and 1134 (formed in the base 1136) and into the venturi 1126 (also formed in the base 1136). In the venturi 1126, the fluid 1130 is mixed with pressurized gas and is discharged from the venturi 1136 as an aerosol through the venturi outlet opening 1138. The fluid then passes through a series of vortex chamber housings for breaking down into smaller particles and further vaporizing any non-vaporized or partially vaporized particles in the flow. Lastly, the fluid is output from the system through the system output 1128.

Specifically, as shown in FIG. 33, the compressible container 1122 is illustrated as comprising a bag having a flexible side wall 1140 and a flexible base 1142. The flexible wall 1140 and flexible case 1142 define a hollow interior 1144 within the compressible container 1122. As the compressible container 1122 is compressed, the volume of the hollow interior of 1144 is reduced, thus increasing the pressure within the hollow interior 1144.

A compressible fluid container output port 1160 is defined by an interior surface 1161 of a connector 1148. Advantageously, the connector 1148 is formed of a pliable material, such as rubber. The connector 1148 is coupled with the base 1136 via a barbed connector 1150. The barbed connector 1150 is shown as comprising a threaded portion 1152, a shoulder 1154, and a barbed extension 1156. A raised barb 1158 is formed on the extension 1156 to allow a resistance or interference fit between the barbed connector 1150 and the connector 1148 of the container. The barbed connector 1150 further comprises a passageway 1159 extending from the output port 1160 to the conduit 1132 to permit the fluid 1130 within the hollow interior 1144 of the compressible container 1122 to pass from the container 1122 into the conduit 1132. Accordingly, in the assembled configuration shown in FIGS. 32 and 33, the threaded portion 1152 of the connector 1150 is threadedly engaged with the base 1136. The compressible container 1122 is, in turn, removably secured by a resistance or an interference fit with the barbed connector 1150 by pressing the pliable connector 1148 over the extension 1156 so that a tight resistance or interference fit is created between the barbed extension 1156 and the interior surface 1161 of the connector 1148.

The compressible container 1122 is shown as being positioned within a pressure chamber 1164 defined by an interior surface 1166 of a pressure housing 1168. The pressure housing 1168 is secured to the base 1136 by threads 1170 formed on one end of the pressure housing 1168 for threadedly engaging the pressure housing 1168 with the base 1136. To create a substantially airtight seal between the base 1136 and the housing 1168, a gasket, such as an O-ring 1172, is positioned, and preferably compressed, between a flange 1174 of the housing 1168 and a contact surface 1176 of the base 1136.

The pressure chamber 1164 is pressurized by receiving pressurized gas from the source of pressurized gas 1124 through a pressurized gas conduit 1178. The source of pressurized gas may advantageously be coupled with any of a variety of suitable devices, such as a pump or tank of pressurized gas. Further, the pressurized gas may comprise air, oxygen, nitrous oxide or any other suitable gas.

The pressurized gas conduit 1178 is shown as being formed in the base 1136 and as extending from venturi inlet opening 1180 to the pressure chamber 1164. By passing pressurized gas through the conduit 1178 into the pressure chamber 1164, the pressure within the pressure chamber 1164 increases. This increase of chamber pressure causes the compressible container 1122 to compress, thus squeezing the fluid 1130 out of the container 1122 through the output port 1160 and the connector passageway 1159.

As shown in FIG. 33, the contents of the compressible container 1122 may comprise liquefied fluid 1130 and, in some instances, an amount of gas-phase fluid, such as air 1182. The system 1120 may be used to vaporize a wide range of fluids. In one embodiment, the liquefied fluid 1130 to be vaporized comprises a medicinal preparation to be administered to a patient by inhalation. Preferably, as the fluid exits the system through the system output 1128, only a small percentage of the non-vaporized fluid particles are greater than five microns in size. By vaporizing a fluid medicinal preparation by passing it through the system 1120, the medicinal preparation may be effectively administered to a patient by inhalation.

A flow regulator or ball valve assembly 1184 is coupled to the fluid conduit 1132 extending from the output port 1160. The flow regulator 1184 is shown as generally comprising a regulator housing 1186, a ball 1188 which seats into an appropriately sized cavity, an adjustment screw 1190, and a bias member 1192. The flow regulator housing 1186 is removably secured to the base 1136 by a threaded engagement. As shown, the ball 1188 seats within a spherical opening 1194 formed in the base 1136. The ball 1188 is biased against the spherical opening 1194 by means of a bias member 1192. As illustrated in FIG. 33, the bias member 1192 may comprise a conventional coil spring. In this configuration, as the pressure within the hollow interior 1144 of the compressible container 1122 increases, the pressure within the conduit 1132 increases correspondingly, thus overcoming the bias and pushing the ball 1188 away from the spherical opening 1194 to permit fluid to pass by the ball 1188 from the conduit 1132 into the conduit 1134.

The amount of pressure necessary to unseat the ball 1188 from the spherical opening 1194 may be adjusted by adjusting the compression of the bias member 1192. The compression, and thus the force exerted by the bias member 1192, is readily adjusted by advancing or withdrawing the adjustment screw 1190 relative to the housing 1186. The farther the screw 1190 is advanced into the housing 1186, the more compressed the bias member 1192 will be and, consequently, the more pressure will be required to unseat the ball 1188 to permit fluid to pass by the regulator assembly 1184. Conversely, as the screw 1190 is withdrawn from the housing 1186, the compression of the bias member 1192 is decreased, and thus a lesser pressure within the conduit 1132 will be required to unseat the sphere 1188.

The ball valve assembly 1184 is only one of many different regulators that can be effectively used to control the flow of fluid between the conduits 1132 and 1134. It is to be understood that any suitable valve or other flow-regulating devices may be effectively employed.

In addition to supplying pressurized gas to the pressurized gas conduit 1178, the source of pressurized gas 1124 also feeds pressurized gas into the venturi 1126 through a venturi inlet opening 1180. The venturi 1126 generally comprises the venturi inlet opening 1180, a venturi outlet opening 1196, and a narrow throat portion 1198. The narrow throat portion 1198 is shown as being positioned between the venturi inlet opening 1180 and the venturi outlet opening 1196.

As a flow F of pressurized gas from the pressurized gas source 1124 passes through the venturi 1126, the narrow throat portion 1198 causes the velocity of the pressurized gas to substantially increase. The high speed of the gas through the venturi throat portion 1198 creates a low pressure region at the venturi throat portion 1198. As shown, the narrow throat portion 1198 is in fluid communication with the conduit 1134. The low pressure region at the narrow throat portion 1198 helps to draw fluid from the conduit 1134 into the high-speed, low-pressure gas flow through the venturi throat portion 1198. As the fluid 1130 passes through the conduit 1134 into the narrow throat portion 1198, the fluid 1130 is mixed with the pressurized gas from the pressurized gas source 1124. Because of the high velocity of the gas passing through the narrow throat portion 1198 and the pressure differentials created by the venturi 1126, the fluid 1130 advantageously exits the venturi 1126 through the venturi outlet opening 1196 as an aerosol.

After exiting the venturi 1126, the fluid is discharged into a mixing chamber 1200 through a plurality of apertures 1202 formed in a hollow boss 1204. As shown in FIG. 33, the boss 1204 is formed as one piece with the base 1136 and comprises a hollow interior 1206 in fluid communication with the venturi outlet opening 1196. Thus, upon exiting the venturi 1126 through the venturi outlet opening 1196, the fluid passes into the mixing chamber 1200 through the apertures 1202 formed in the boss 1204.

The mixing chamber 1200 is defined by a base exterior surface 1210, an inside surface 1212 of a tube 1214, and the exterior surface 1216 of the venturi chamber housing 1128. The vortex chamber housing 1128 is configured and functions in the same manner as the vortex chamber housing 940 described above and illustrated in FIG. 23.

As shown in FIG. 33, the vortex chamber housing 1128 further comprises an exterior bottom surface 1220 which is positioned adjacent to and abuts the boss 1204, causing the fluid passing through the boss hollow interior 1206 to exit the hollow interior through the apertures 1202. After the flow F of fluid enters the mixing chamber 1200, the fluid next passes into the vortex chamber 1124 through tangential apertures 1220 formed in the vortex chamber housing 1128. The tangential slots 1222 are identical to the elongated tangential slots 950 described above and illustrated in FIG. 23. The tangential slots 1222 permit the fluid to be directed tangentially into the vortex chamber 1224. Due to the tangential orientation of the slots 1222, the fluid is directed tangentially into the vortex chamber 1224 to create a vortical flow of fluid within the vortex chamber 1224.

An output fixture 1230 is attached to the vortex chamber housing 1128 for directing the fluid from the vortex chamber 1224 into a mixing chamber 1232. The output fixture 1230 is illustrated as being attached to the vortex chamber housing 1128 by a press-fit attachment, but could also be secured to the vortex housing by a number of conventional methods.

The output fixture 1230 is shown in FIG. 33 as comprising a body 1234 having an annular groove 1236 formed about the periphery of the body 1234. A gasket, such as O-ring 1238, may be positioned within the groove 1236 to prevent the fluid from passing directly from the mixing chamber 1200 to the mixing chamber 1232 without passing through the vortex chamber 1224. The output fixture 1230 further comprises a hollow interior 1240 and apertures 1242 for directing the fluid from the vortex chamber 1224 through the output fixture 1230 into the mixing chamber 1232. Upon exiting the output fixture 1230 through the apertures 1242, the fluid passes through the mixing chamber 1132 and through the vortex chamber housing 1244 in the same manner as the fluid passes through the vortex chamber housing 1128. Likewise, the fluid exits the vortex chamber housing 1244 through an output fixture 1246 which is configured identical to the output fixture 1230 discussed above and illustrated in FIG. 33. In this same manner, as shown in FIG. 32, the fluid passes through the vortex chambers 1248, 1250, 1252, 1254, 1256, and 1258 as well as through output fixtures 1260, 1262, 1264, 1266, 1268, and 1270. As shown, the vortex chamber housings 1244, 1248, 1250, 1252, 1254, 1256, and 1258 are each configured and function in a manner identical to that of the vortex chamber housing 1128. Likewise, the output fixtures 1246, 1260, 1262, 1264, 1266, 1268, and 1270 are configured and function in a manner identical to that of the output fixture 1230 described above and illustrated in FIG. 33. Accordingly, no further description of these features is necessary.

Upon exiting the output fixture 1270 (FIG. 32), the fluid enters a discharge chamber 1272 defined by the output fixture 1270 and an inside surface 1274 of an output housing 1276. As shown, the output housing 1276 is rigidly secured to the tube 1214. The inside surface of the output housing 1276 while the discharge housing 1276 is illustrated as being attached to the tube 1214 by a press-fit attachment, the discharge housing 1276 could also be affixed to the tube 1214 by a variety of methods, including adhesion or a threaded engagement.

The discharge housing 1276 further comprises a plurality of output channels 1278 for passing the fluid from the discharge chamber 1272 into a discharge orifice 1280. The discharge orifice 1280 further comprises a threaded portion 1282 to permit a conventional threaded connector such as a hose nipple 1284 to be threaded into the discharge housing 1276 for receiving fluid from the discharge aperture 1280. An output end 1285 of the conventional connector 1284 may conveniently be coupled to a variety of fluid receiving devices, such as inhalation mouthpieces, or other structures for receiving a substantially vaporized flow of the fluid 1130.

The operation of the embodiment illustrated in FIGS. 1–6 is described below. Liquid, such as fuel, is electronically controlled, metered, and sprayed as an aerosol through the output ports 46 of the fuel injectors 38 into the preliminary mixing chamber 44. While fuel is the fluid referred to herein, other fluids, such as medicine and waste liquid may also be vaporized and homogenized using the devices and methods disclosed.

As fuel is sprayed into the preliminary mixing chamber 44, the throttle plate 84 opens to permit an amount of air to be input into the venturi 82. The amount of air permitted to pass by the throttle plate 84 is proportional to the amount of fluid sprayed into the preliminary mixing chamber by the output ports 46 of the fuel injectors 38. An engine-created vacuum pulls the fluid from the mixing chamber 44 through the apertures 66 formed in the chamber housing 54.

When the engine operates, a partial vacuum is produced in the engine intake manifold (not shown). With the throttle plate in a closed position, the lower pressure air/fuel mixture in the preliminary mixing chamber 44 is drawn tangentially through the apertures 66 into the vortex chamber 64. Specifically, air for the vortex chamber is introduced through the slot 94 and passes through the ambient air channel 100 and the conduit 102 into the ambient air conduit 50. From the ambient air conduit 50, ambient air is introduced into the preliminary mixing chamber where the ambient air mixes with the aerosol fuel prior to entering the apertures 66 as an air/fuel mixture.

The air/fuel mixture is introduced substantially tangentially into the vortex chamber 64 where the fluid is rotationally accelerated due to incoming fluid through the apertures 66. The amount of fluid entering the various apertures 66 is substantially equalized by the presence of the jacket 60. The inside surface 56 of the jacket restricts the flow of fluid entering the apertures according to the location of the aperture relative to the output port 70, which comprises a low pressure end of the flow passing through the vortex chamber 64. Essentially, the jacket provides a heightened restriction on apertures closer to the output port 70 and a lesser, if any, restriction of the apertures farthest from the low pressure end (output port 70).

Once the fluid is inserted into the vortex chamber 64, the fluid is rotationally accelerated, which causes any non-vaporized particles of fluid within the flow to break down into smaller particles, to be vaporized, or both. When the fluid reaches the output port 70, the fluid passes from the chamber 64 into the intermediate chamber 136 as a spinning column of fluid. In the intermediate chamber 136, the fluid is enfolded upon itself, thus breaking up the spinning column of fluid and creating additional turbulence and homogenization of the flow.

The flow is then drawn by the partial vacuum created by the engine manifold through the elongated apertures 106 of the venturi 82. The elongated apertures 106 are significantly larger and more numerous than conventional small circular venturi chamber apertures as they are designed to reduce any pressure drop and to enable a flow of up to 60 CFM. In the venturi 82, the ambient air, admitted by the throttle plate 84, is mixed with the air/fuel mixture as the air/fuel mixture enters through the apertures 106. The ambient air/fuel mixture is further mixed, and at least partially homogenized, within the venturi 82.

The partial vacuum of the engine manifold next draws the fluid through the centrifuge intake opening 144 as the fluid enters the entry chamber 146. The entry chamber serves to further mix and homogenize the fluid and to direct the fluid into the centrifuge chamber 152 tangentially. Specifically, the baffles 150 formed within the entry chamber 146 create a series of tangential passageways 200, 202, and 204 through which the fluid is tangentially drawn into the centrifuge chamber 152 by the partial engine manifold vacuum.

In the centrifuge chamber 152, the fluid is rotationally accelerated which causes the largest or heaviest particles to be moved, due to their mass, toward the perimeter of the centrifuge chamber 152 where these heavier, or more massive, particles collide with the interior surface 156 and are further broken down and vaporized.

To reduce the volume of the centrifuge chamber 152, it is advantageous that the height of the side wall 156 be smaller than the inside diameter 114 of the venturi 82 at the venturi output 110. Additionally, to reduce the volume of the centrifuge chamber 152 and to enhance the centrifugal flow in the chamber 152, the extension member 162 extends from the centrifuge housing top wall 160.

The fluid is then drawn into the four outputs 154 by the engine vacuum. As the lighter particles of the flow centrifugally advance toward the center of the centrifuge housing 152, they are directed, at an angle, by the conically-shaped portion of the centrifuge contoured top surface 170 into the apertures 182 formed in the conically-shaped portion 180 and into the four outputs 154. By discharging the fluid from the centrifuge chamber in the manner described, a more uniform hydrocarbon distribution is obtained due to the hydrocarbon's generally tendency to be positioned towards the outside of the centrifugal flow in the centrifuge chamber. In contrast, where only one output port is employed, the centrifuge discharge is less uniform due to the tendency of hydrocarbons to be positioned toward the outside of the centrifugal flow.

Turning now to the embodiment of the invention illustrated in FIG. 7, the vortex configuration 220 is supplied with aerosol fuel by fuel injectors 222. The fuel injectors 222 spray fuel into a preliminary mixing chamber 242. Ambient air is also introduced into the preliminary mixing chamber 242 via the ambient air conduit 244. In the preliminary mixing chamber, the aerosol fuel and the ambient air are mixed so as to enter the vortex chamber 248 through the apertures 260 as an air/fuel mixture.

In a manner similar to the jacket 60 (FIG. 1), the jacket 272 serves as a pressure differential supply to normalize the amount of flow through the various apertures 260. The air/fuel mixture enters the vortex chamber 248 through the apertures 216 in a manner similar to that described in connection with the vortex chamber 54 and aperture 66 of FIG. 1. As the air/fuel mixture exists the U-shaped output port 340, the mixture enters into a mixing chamber 350 prior to entering the vortex chamber 250 through apertures 262. In this configuration, the apertures 262 receive the air/fuel mixture exclusively from the output from the vortex chamber 248 to maintain a substantially constant air/fuel ratio as the air/fuel mixture passes through the chambers 248 and 250.

Subsequently, the air/fuel mixture exits the U-shaped output port 242 and enters into mixing chamber 352 prior to entering the vortex chamber 252 through apertures 264. Again, the air/fuel ratio of the air/fuel mixture remains substantially constant as the fluid passes through the vortex chambers 250 and 252.

After exiting the output port 344 of the chamber housing 228, the fluid continues to pass through the mixing chamber 354, apertures 266, and vortex chamber 254 in a manner identical to that described in connection with the vortex chamber 252. Upon exiting the U-shaped output port 346, the fluid enters the mixing chamber 356, passes through the apertures 268 into the final chamber 256 prior to exiting the output port 348.

By passing through the five chambers 248–256, the fluid becomes increasingly vaporized and transformed in a gaseous phase as it advances from one chamber to the next. Accordingly, this embodiment permits an air/fuel mixture to pass through several vortex chambers while maintaining a substantially constant air/fuel ratio.

Turning now to the embodiment illustrated in FIGS. 15–17, fuel is injected into a first chamber 426 from a conventional fuel injector 424. Air is then introduced into the chamber through apertures 436 to rotationally accelerate the fluid. As the fluid advances from the chamber 428 to the chamber 430, it passes through a nozzle 490 which causes the fluid to undergo additional differentials in pressure to enhance the vaporization of the fluid. The fluid continues to advance through the various chambers 430–434 and nozzles 488 and 486. When the fluid reaches the output port 484, it is introduced to an elongated conduit 478, through which the fluid passes until it reaches the output 479.

To alleviate the problems of acceleration stumble, the elongated conduit 478 is selectively passed through the chambers 430–434 into direct communication with the nozzle 490 to selectively isolate the chamber 428 and to permit the fluid to bypass chambers 430–434.

When accelerating, the solenoid 476 is energized, which causes the conduit base 480 to slide along the interior surface 466 of the tube portion 456, compressing the spring 482 and advancing the bypass conduit 478 into direct communication with the chamber 428. In most instances, the period of insertion will be on the order of 0.5 seconds.

After the fluid has exited the output 479, it enters the venturi 506 and is passed into the centrifuge chamber through the output channel 532. Then, after spinning centrifugally in the centrifuge chamber 542, the fluid is discharged through output 548 into the engine manifold (not shown).

The embodiment illustrated in FIG. 20 permits the effective cross-sectional area of the output 660 to be selectively varied. In operation, the stepper motor advances and retracts the conical plug 678 relative to the output 660. Thus, as the conical plug is moved relative to the output, the effective cross-sectional area of the output may be selectively varied.

An alternate embodiment of a vortex chamber housing is illustrated in FIG. 23. In operation, the vortex chamber housing 940 receives fluid through the tangential slots 950 into the chamber interior 952 to create a vortical flow of fluid within the chamber interior 952. The elongated slots 950 introduce the fluid tangentially into the chamber interior as a sheet of fluid along the interior surface 946 of the vortex chamber housing to prevent liquid particles from congregating on the interior surface 946. As the fluid spins vortically within the chamber 952, the pressure differentials and the overall turbulence of the flow within the chamber 952 cause the fluid to be vaporized and homogenized.

FIGS. 24 and 25 illustrate an alternative embodiment of a venturi 956 formed in accordance with the principles of the present invention. In operation, the venturi 956 receives a flow of fluid through the venturi inlet opening 962. This flow of fluid is then mixed with an air/fuel mixture which enters the venturi interior 960 through tangential apertures 958 formed in the wall 956 to create a helical flow of fluid through the venturi 954. Introducing the air/fuel mixture tangentially into the venturi interior 960 causes the flow through the venturi 954 to spin helically. Advantageously, the air/fuel mixture is introduced in the narrow throat portion 959 of the venturi interior 960 because the narrow throat portion 959 comprises the region of fastest air flow within the venturi 954. By creating a helical flow of fluid through the venturi 956, the turbulence, and thus the vaporization and homogenization, of the fluid is substantially enhanced.

FIGS. 26–30 illustrate a yet additional embodiment of a centrifugal vortex system 970. As shown in FIGS. 27 and 28, in this embodiment, fuel is sprayed into the preliminary mixing chamber 976 by the fuel injectors 974. The air/fuel mixture is then tangentially introduced to the vortex chamber 990 through an array of tangential apertures 992 formed in the vortex chamber housing 978. The air/fuel mixture is then output through output port 994.

When the engine is at idle, the secondary throat 977 is substantially sealed by the conical plug 1012 being engaged with the aperture 1010. Additionally, the secondary throttle plate 1032 (FIG. 29) is in a closed position. Further, while the engine is at idle, the primary conical plug 1000 is raised a distance above the aperture 996 so as to permit a small flow of the air/fuel mixture to pass from the output port 994 into the primary throat 973. At idle, the primary throttle plate 1030 (FIG. 29) is closed. Then, as the engine speed is increased from idle, the primary linear actuator 978 moves the conical plug away from the aperture 996 to permit a greater amount of air/fuel mixture to pass through the aperture 996 into the primary throat 973. Simultaneously, the primary throttle plate 1030 begins to open to increase the amount of air/fuel mixture admitted to the engine.

With reference to FIGS. 26 and 30, as the primary throttle plate 1030 continues to open, the primary arm 1044 rotates in a clockwise direction causing the link 1046 to advance through the slot 1052 formed in the secondary arm 1048. When the primary throttle plate 1032 has been opened to a predetermined position, such as approximately 40% open, the link 1046 contacts the end 1054 of the slot 1052 and the link 1046 begins to cause the secondary arm 1048 to rotate. The rotation of the secondary arm 1048 then begins to open the secondary throttle plate 1032 by rotating the shaft 1036.

Simultaneously with the opening of the secondary throttle plate 1032, the secondary linear actuator 981 disengages the conical plug 1012 from the aperture 1010 to permit flow through the passageway 1111. Thus, as the primary throttle plate 1030 continues to open past the predetermined position, the secondary throttle plate 1032 opens and the passageway 1111 is opened to allow flow through both the primary and secondary throats 973 and 977 to enhance the volumetric efficiency of the system 970.

As the primary throttle plate 1030 continues to open, the linkage assembly 1042 continues to cause the secondary throttle plate to open such that when the primary throttle plate 1030 is fully open, the secondary throttle plate 1032 is also fully open. When the primary and secondary throttle plates 1030 and 1032 are fully open, the conical plugs 1000 and 1012 are fully retracted to maximize the flow through the primary and secondary throats 973 and 977 to enhance volumetric efficiency. Then, as the engine speed is decreased, the primary throttle plate 1032 begins to close, thus causing the secondary throttle plate 1032 to also begin to close. As the secondary throttle plate begins to close, the conical plug 1012 is moved closer to the aperture 1010 to restrict fluid flow through the passageway 1111 into the secondary throat 977. When the primary throttle plate 1030 is repositioned at the predetermined location, the secondary throttle plate is completely closed and the conical plug 1012 is reinserted within the aperture 1010 to seal off the secondary throat 977 and to isolate the primary throat 973, thus providing a high resolution response. As the engine speed is further decreased toward idle, the flow through the primary throat 973 is further reduced by continuing to close the primary throttle plate 1030 and moving the primary conical plug 1000 into close proximity with the aperture 996.

Thus, in the configuration illustrated in FIGS. 26–30, both high resolution response and volumetric efficiency are attainable. The high resolution response is achieved at low engine speeds by isolating the flow within the primary throat 973. At high engine speeds, where volumetric efficiency is desirable, the secondary throat 977 is opened and used in combination with the primary throat 973.

FIG. 31 illustrates an embodiment similar to that illustrated in FIGS. 26–30 and described above. The primary difference between the embodiment illustrated in FIG. 31 and that illustrated in FIGS. 26–30 is that the embodiment of FIG. 31 is designed for a four barrel system whereas the embodiment illustrated in FIGS. 26–30 is intended for a two barrel system.

In operation, the embodiment illustrated in FIG. 31 receives an air/fuel mixture into the primary and secondary throats from the vortex chamber assemblies 1060 and 1062 in a manner identical to that described above in the embodiment illustrated in FIGS. 26–30. The embodiment of FIG. 31 operates essentially in the same manner as the embodiment illustrated in FIGS. 26–30 except that there are two secondary throats and two primary throats instead of only one primary and secondary throat as illustrated in FIGS. 26–30.

The linkage assembly 1100 illustrated in FIG. 31 is configured and operates in a manner identical to that of the linkage assembly 1042 illustrated in FIGS. 26 and 30. The primary shaft 1090 controls the primary throttle plates 1080 and 1082 and the secondary shaft 1094 controls the throttle plates 1084 and 1086. In a manner similar to that illustrated in FIGS. 26–30 and described above, as the primary throttle plates 1080 and 1082 are opened, the primary linear actuators move conical plugs within the primary throats to permit a flow of fluid through each primary throat. Then, as the linkage assembly 1100 causes the secondary throttle plates 1084 and 1086 to open, the secondary linear actuators 1068 and 1070 move conical plugs within the secondary throats to permit fluid to flow through the primary and secondary throats to enhance volumetric efficiency. Likewise, as the throttle plates close, the respective linear actuators also move the conical plugs to enhance a high resolution response.

As discussed above, FIGS. 32 and 33 illustrate a yet additional embodiment of the invention. In this embodiment, positive pressure is provided into the system 1120 through a positive pressure source 1124 which delivers gas, under pressure, into the venturi inlet opening 1180 and into the pressurized gas conduit 1178. The pressurized gas passes through the pressurized gas conduit 1178 into the pressure chamber 1164. As the pressure within the pressure chamber 1164 increases due to the pressurized gas, the compressible container 1122 is compressed, thus reducing the volume and increasing the pressure of the container of hollow interior 1144. As the compressible container 1122 is compressed, the fluid 1130 within the container 1122 is forced out of the container 1122 through the output port 1160, through the passageway 1159, and into the fluid conduit 1132.

The flow of fluid from the fluid conduit 132 to the conduit 134 is controlled by the regulator 1184. In the biased position illustrated in FIG. 33, the sphere 1188 is biased against the spherical seat 1194 to prevent fluid from flowing from the conduit 1132 to the conduit 1134. As the pressure within the conduit 1132 increases, however, the bias against the spherical seat 1194 is overcome and the sphere 1188 is dislodged from the spherical seat 1194 to permit the fluid to pass from the conduit 1132 to the conduit 1134.

The bias of the sphere 1188 against the spherical seat 1194 can be adjusted by advancing or withdrawing the screw 1190 within the housing 1186. As the screw 1190 is advanced into the housing 1186, the spring 1192 is compressed, thus increasing the bias on the sphere 1188. Conversely, as the screw 1190 is withdrawn from within the housing 1186, the spring 1192 is decompressed, thus reducing the amount of bias on the sphere 1188. With a reduced bias on the sphere 1188, a lesser pressure in the conduit 1132 is required to unseat the sphere 1188 and to enable flow from the conduit 1132 to the conduit 1134.

After passing by the regulator 1184, the fluid passes through the conduit 1134 and enters the venturi throat portion 1198 as an aerosol. As the pressurized gas passes through the venturi 1126, the velocity of the gas increases as it passes through the narrow throat portion 1198, thus creating a low pressure region at the narrow throat portion 1198. The low pressure associated with the high velocity flow through the venturi narrow throat portion 1198 helps to draw the fluid through the conduit 1134 into the narrow throat portion 1198.

In the venturi throat portion 1198, pressurized gas from the source of pressurized gas 1124 is mixed with the fluid 1130. After mixing with the pressurized gas, the fluid exits the venturi 1126 through the venturi outlet opening 1196 as an aerosol. From the venturi outlet opening 1196, the fluid passes through apertures 1202 formed in the boss extension 1204 and into the mixing chamber 1200. From the mixing chamber 1200, fluid enters the vortex chamber 1224 through the tangential slots 1222 to create a vortical flow within the vortex chamber 1224 for breaking down into smaller particles and vaporizing any non-vaporized particles in the vortical flow.

The fluid then passes from the vortex chamber 1224 into the mixing chamber 1232 through the apertures 1242 formed in the output fixture 1230. The fluid continues to pass through the subsequent vortex chamber housings 1244, 1248, 1250, 1254, 1256, and 1258 as well as through subsequent output fixtures 1246, 1260, 1262, 1264, 1266, 1268, and 1270 in the same manner as the fluid passes through the vortex chamber housing 1128 and the output fixture 1230 respectively. The fluid is further homogenized and vaporized through each succeeding vortex chamber housing.

Upon exiting the final output fixture 1270, the fluid passes through a discharge chamber 1272 and into the channels 1270 to supply the output orifice 1280 with a supply of substantially vaporized fluid. To facilitate the delivery of the vaporized fluid to its final destination, the fluid may pass through a conventional hose connector 1284.

The various systems and methods described have been directed to the vaporization and homogenization of fuel for internal and external combustion engines. The inventor appreciates that the devices and methods disclosed in this document have applicability in connection with the preparation of other fluids. For example, the present systems and devices may be employed in connection with preparing a medication to be administered to a patient by inhalation through the lungs into the bloodstream. In the past, it has been difficult to sufficiently break down and vaporize a medication into particles small enough to pass directly into the bloodstream through a patient's lungs. The systems and methods disclosed in this document have applicability in alleviating that need.

The systems and methods disclosed in this documents are also applicable and useful in the breakdown, vaporization, and homogenization of waste fluids for incineration and waste management. As the waste fluid particles are broken down into extremely small particle sizes, the waste fluid introduced into an incinerator will be burned more efficiently, thereby minimizing pollution and increasing the efficiency of which the waste fluids are incinerated.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications with the proper scope of the appended claims appropriately interpreted in accordance with the doctrine of equivalents.

What is claimed is:

1. A centrifugal vortex system for vaporizing a fluid, comprising:
   a fluid flow path having a high pressure end and a low pressure end;
   a vortex housing defining a vortex chamber through which a fluid flow is directed, the vortex chamber being positioned along the fluid flow path and interposed between the high pressure end and the lower pressure end to permit a fluid to flow from the high pressure end to the low pressure end;
   a plurality of input apertures formed in the vortex housing to allow the input of fluid tangentially into the vortex chamber for vaporizing the fluid;
   wherein the apertures are located at different distances relative to the low pressure end;
   a pressure differential supply associated with the input apertures to allow a differential pressure of fluid at the input apertures according to the location of the apertures relative to the low pressure end;
   an ambient air supply coupled to the vortex chamber.

2. A vortex system for vaporizing a fluid according to claim 1 wherein the plurality of input apertures are arranged in a plurality of rows and a plurality of columns.

3. A vortex system for vaporizing a fluid according to claim 1 wherein the pressure differential supply comprises a jacket.

4. A vortex system for vaporizing a fluid according to claim 1 wherein the pressure differential supply comprises a jacket having an increasing diameter inner surface.

5. A vortex system for vaporizing a fluid according to claim 1 wherein the pressure differential supply comprises a jacket having a tapered inner surface.

6. A vortex system for vaporizing a fluid according to claim 1 wherein the pressure differential supply comprises a jacket having an inner surface, the jacket inner surface defining a variable width gap between the jacket inner surface and a vortex housing exterior surface.

7. A vortex system for vaporizing a fluid according to claim 1 wherein the pressure differential supply comprises a jacket having a variable diameter inner surface, the inner surface having a maximum diameter end and a minimum diameter end;
   wherein the minimum diameter end is positioned adjacent to an aperture closer to the low pressure end to reduce a tendency of the aperture closer to the low pressure end to receive more flow than an aperture located farther from the low pressure end.

* * * * *